US008106003B2

(12) United States Patent
Krissansen

(10) Patent No.: US 8,106,003 B2
(45) Date of Patent: Jan. 31, 2012

(54) PEPTIDES AND METHODS FOR THE TREATMENT OF INFLAMMATORY DISEASE

(75) Inventor: Geoffrey Wayne Krissansen, St. Johns (NZ)

(73) Assignee: Auckland Uniservices Limited, Auckland (NZ)

( * ) Notice: Subject to any disclaimer, the term of this patent is extended or adjusted under 35 U.S.C. 154(b) by 435 days.

(21) Appl. No.: 11/575,026

(22) PCT Filed: Sep. 9, 2005

(86) PCT No.: PCT/NZ2005/000234
§ 371 (c)(1),
(2), (4) Date: Sep. 25, 2007

(87) PCT Pub. No.: WO2006/028393
PCT Pub. Date: Mar. 16, 2006

(65) Prior Publication Data
US 2009/0181900 A1    Jul. 16, 2009

(30) Foreign Application Priority Data
Sep. 9, 2004 (AU) .............................. 2004905153

(51) Int. Cl.
A61K 38/08 (2006.01)
A61K 38/10 (2006.01)
C07K 7/06 (2006.01)
C07K 7/08 (2006.01)

(52) U.S. Cl. ....... 514/1.2; 514/21.5; 514/21.8; 530/327; 530/329

(58) Field of Classification Search .................. None
See application file for complete search history.

(56) References Cited

U.S. PATENT DOCUMENTS

| 5,922,570 | A | * | 7/1999 | Staunton et al. | 435/69.2 |
| 6,077,822 | A | * | 6/2000 | Dyrsting et al. | 514/8 |
| 6,274,556 | B1 | * | 8/2001 | Schwender et al. | 514/17 |
| 2003/0054000 | A1 | * | 3/2003 | Dowdy | 424/94.63 |
| 2003/0105000 | A1 | * | 6/2003 | Pero et al. | 514/12 |
| 2004/0123343 | A1 | | 6/2004 | La Rosa et al. | |

FOREIGN PATENT DOCUMENTS

| WO | WO 97/14432 | | 4/1997 |
| WO | WO 0015243 A1 | * | 3/2000 |
| WO | 01/79144 | | 10/2001 |
| WO | WO 01/79144 A2 | * | 10/2001 |
| WO | WO 02/051993 | | 7/2002 |

OTHER PUBLICATIONS

Dubree et al. Selective alpha4/beta7 Integrin Antagonists . . . Journal of Medicinal Chemistry. 2002, vol. 45, No. 16, pp. 3451-3457.*
Micklem et al. HML-1 Antigen on Mucosa-associated T cells . . . American Journal of Pathology. Dec. 1991, vol. 139, No. 6, pp. 1297-1301.*
Plosker, et al; Eptifibatide "A Pharmacoeconomic Reviwe of its Use in Percutaneous Coronary Intervention and Acute Coronary Syndromes", Pharmacoeconomics 2003:21 (12): 885-912.
Liu, et al; Lotrafiban: an oral platelet glycoprotein IIb/IIIa blocker; Exp. Opin. Invest. Drugs (2000) 9(11):2673-2687.
Andronati, SA et al: "Peptidomimetics—antagonists of the fibrinogen receptors: molecular design, structures, properties and therapeutic applications", Curr Med Chem, May 2004, 11(9), pp. 1183-1211.
Ruoslahti, E.: "RGD and other recognition sequences for integrins", Annu Rev Cell Dev Biol. 1996; 12, pp. 697-715.
Raja, PV et al: "Cognitive deficits following coronary artery bypass grafting: prevalence, prognosis, and therapeutic strategies", CNS Spectr., Oct. 2004; 9(10), pp. 763-772.
Pals, S T et al: "Expression of themucosal homing receptor alpha 4 beta 7 in malignant lymphomoatous polyposis of the intestine" Gastroenterology, Nov. 1994, 107(5), pp. 1519-1523.
Geissmann, F et al: "Homing receptor alpha4beta7 integrin expression predicts digestive tract involvement in mantle cell lymphoma", Am J Pathol, Dec. 1998, 153(6), pp. 1701-1705.
Agrez, M V, "Integrin-binding domain of mitogen-activated protein kinases and its use for modulating cellular activity in cancer and other cells", Chemical Abstract Accession No. RN 439760-32-4. Abstract of WO 2002/051993 (Jul. 4, 2002).
Philips, D et al; "Modulation of integrin-mediated signal transduction", Chemical Abstract Accession No. 126:338883; 1/9/3 Dialog(R) File 399:CA Search (R) (c) 2007 America Chemical Society. Abstract of WO 97/14432 (Apr. 24, 1997).
Vivien Marx, C & EN Northeast News Bureau; Various Articles and Discussions Obtained from the Internet; File No. 503963NZPR (2005).
Dolcetti, et al, "α4β7 Integrin Expression is Associated with the Leukemic Evolution of Human and Murine T-Cell Lymphoblastic Lymphomas", American Journal of Pathology: vol. 150. No. 5, May 1997: p. 1595-1605.
Yuan QA et al., "Cloning and sequence analysis of a novel beta 2-related integrin transcript from T lymphocytes: homology of integrin cysteine-rich repeats to domain III of laminin B chains", Int. Immunol. 1990:2(11):1097-108. Erratum in: Int. Immunol. Dec. 1991:3(12):1373-4.
Yuan Q. et al., "Molecular cloning of the mouse integrin beta 7 subunit", J. Biol. Chem. Apr. 15, 1992:267(11):7352-8. Kanwar, et al; β7 integrins contribute to demyelinating disease of the central nervous system; Journal of Neuroimmunology 103 (2000) 146-152, Elsevier Science B.V.
Krissansen, et al, A pseudosymmetric cell adhesion regulatory domain in the β7 tail of the integrin α4β7 that interacts with focal adhesion kinase and src; European Journal of Immunology 2006. 36: 2203-2214.

* cited by examiner

*Primary Examiner* — Jeffrey E Russel
(74) *Attorney, Agent, or Firm* — Occhiuti Rohlicek & Tsao LLP

(57) ABSTRACT

The invention relates to isolated peptides comprising at least the amino acid sequence YDRREY (SEQ ID NO:1) or a derivative thereof, nucleic acid encoding the peptides, pharmaceutical compositions and methods for modulating β 7 integrin function, including methods for treatment of inflammatory disorders, antibodies directed to the peptides and methods for identification of integrin β7 functional interactors.

27 Claims, 12 Drawing Sheets

A No peptide β7-2

β7-3

Figure 1:
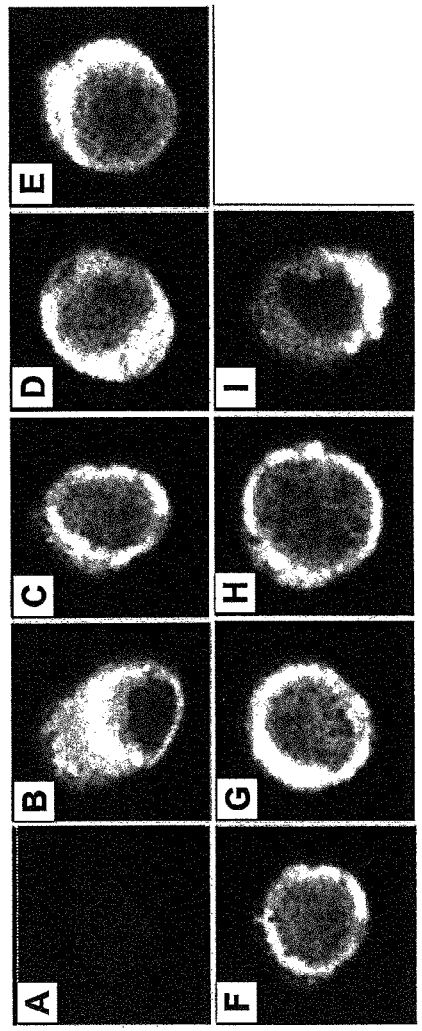

```
β7M  RLSVEIYDRREYRRFEKEQQQLNWKQDNNPLYKSAITTTVNPRFQGTNGRSPSLSLTREAD
β7H  RLSVEIYDRREYSRFEKEQQQLNWKQDSNPLYKSAITTTINPRFQEADSPTL
β6   KLLVSFHDRKEVAKFEAERSKAKWQTGTNPLYRGSTSTFKNVTKHREKQKVDLSTDC
β5   KLLVTIHDRREFAKFQSERSRARYEMASNPLYRKPISTHTVDFTFNKFNKSYNGTVD
β3   KLLITIHDRKEFAKFEEERARAKWDTANNPLYKEATSTETNLLYRGI
β2   KALIHLSDLREYRRFEKEKLKSQWNND NPLFKSATTTVMNPKFAES
β1   KLLMIIHDRREFAKFEKEKMNAKWDTGENPLYKSAVTTVVNPKYEGK
```

FIGURE 10

PEPTIDES AND METHODS FOR THE TREATMENT OF INFLAMMATORY DISEASE

CROSS-REFERENCE TO RELATED APPLICATIONS

This application is the National Stage of International Application No. PCT/PCT/NZ2005/000234, filed Sep. 9, 2005, which claims the benefit of Australian Application Serial No 2004905153, filed on Sep. 9, 2004. The contents of both applications are hereby incorporated by reference in their entirety.

FIELD

The present invention relates to novel peptides, nucleic acids encoding same, pharmaceutical compositions comprising said peptides or nucleic acids, methods for modulating β7 integrin function, including methods for the treatment of inflammatory disorders, antibodies directed to said peptides, and methods for the identification of integrin β7 functional interactors.

BACKGROUND

The precise control of leukocyte adhesivity is critical in maintaining effective homeostasis of the immune response, for lymphocyte motility, homing, and recirculation, the localization of leukocytes at sites of inflammation, and antigen presentation. A small subset of integrins, namely α4, β2, and β7 integrins, largely controls leukocyte adhesion, and related functions (1).

The integrins are a superfamily of transmembrane receptors which mediate cell-extracellular matrix and cell-cell interactions. Each integrin consists of noncovalently paired alpha and beta subunits. There are presently 8 beta and 18 alpha subunits known. The β7 subunit partners with two α chains to form two heterodimeric molecules, namely α4β7 and αEβ7.

Integrin adhesivity is regulated by a complex array of intracellular signalling pathways that impinge on integrin subunit cytoplasmic domains, and trigger changes in integrin conformation, clustering (2), affinity for ligands (3, 4), and cell spreading (5), all of which contribute to increased cell adhesion (6-8).

In the case of β7 integrins, it has been demonstrated that small GTP-binding proteins induce integrin α4β7-mediated T cell adhesion to the mucosal addressin MAdCAM-1 in a hierarchical fashion, by a mechanism predominantly involving changes in receptor avidity due to ligand-induced clustering (9). The control of β7-integrin adhesion is critical as the two β7 integrins, α4β7 and αEβ7, play key roles in forming and maintaining gut immunity (10, 11), and α4β7 contributes to leukocyte infiltration into the islets of Langerhans in Type I diabetes (12), and the central nervous system in demyelinating diseases such as multiple sclerosis (13). α4β7 mediates the adherence of lymphocytes to high endothelial venules (HEV) at such chronically inflamed sites via its preferred ligand MAdCAM-1 (14, 15), whereas αEβ7 mediates the adhesion of intraepithelial lymphocytes to the intestinal epithelium by an interaction with E-cadherin (17,18).

Additionally, "inside-out" transmembrane signalling pathways reveal that the short (~47-66 amino acid residues) integrin β subunit cytoplasmic domains serve as substrates for cellular kinases, and are phosphorylated upon cell activation (19-22). Certain β subunit cytoplasmic domains directly interact with, and share, cytoskeletal elements including talin, α-actinin, paxillin, and filamin. Some share intracellular signalling molecules such as integrin-linked kinase (ILK), and Rack1, yet potentially associate in an exclusive fashion with an array of other intracellular signalling molecules that may ultimately dictate the nature of integrin-specific "inside-out" and "outside-in" signalling pathways. The human WD repeat protein WAIT-1 specifically interacts with the cytoplasmic tails of β7-integrin α and β subunits (β7, α4, and αE), but not those of integrin β1, β2, and αL subunits (23).

Notwithstanding the above knowledge, the nature and identity of the molecules which associate with the integrins and regulate their activity are largely unidentified. Similarly, the regulatory sites or motifs present within the integrin subunits have not been fully characterised. Accordingly, there is still much to be understood of the precise mechanisms which allow for regulation of integrin activity and concomitantly cell-cell or cell-extracellular matrix interactions.

In light of the role integrins play, particularly β7 integrins, in regulating leukocyte activity and targeting, and their implication in the development of certain inflammatory disorders, elucidating the precise mechanisms by which their function may be regulated may allow for control thereof, with concomitant amelioration of relevant inflammatory disorders.

Bibliographic details of the publications referred to herein are collected at the end of the description.

Abbreviations used herein: β7cyt, integrin β7 subunit cytoplasmic domain; CARD, cell adhesion regulatory domain; GST, glutathione S transferase; ICAM-1, intercellular adhesion molecule-1; MAdCAM-1, mucosal addressin cell adhesion molecule-1; PMA, 4β-phorbol 12 myristate 13-acetate; VCAM-1, vascular cell adhesion molecule-1.

OBJECT

It is an object of the present invention to provide novel peptides, nucleic acids encoding same, derivatives of said peptides, pharmaceutical compositions comprising said peptides, derivatives thereof, or nucleic acids, methods for modulating β7 integrin function, including methods for the treatment of inflammatory disorders, antibodies directed to said peptides, and/or methods for the identification of integrin β7 functional interactors and mimetics of said peptides and derivatives thereof.

It is a further, or alternative object to at least provide the public with a useful choice of any one or the above.

STATEMENT OF INVENTION

In accordance with the present invention the inventors have identified a functional motif in the β7 cytoplasmic domain that controls clustering and adhesion of β7 integrins, particularly the integrin α4β7. It has been surprisingly discovered that this functional motif, which encompasses residues 735-740 of the transmembrane-proximal region of the cytoplasmic tail of the β7 subunit, provides a peptide YDRREY (β7-8) (SEQ ID NO. 1) which inhibits the adhesion of β7 integrins to their ligands, as is exemplified hereinafter in relation to α4β7-mediated adhesion of mouse TK-1, and human H9 T cells, to MAdCAM-1, VCAM-1, and RGD-polymer. Peptides carrying the YDRREY (SEQ ID NO. 1) motif, or nucleic acids encoding same, may provide novel anti-inflammatory reagents for the treatment of inflammatory disorders.

Accordingly, in one aspect of the present invention there is provided an isolated peptide comprising at least the amino acid sequence YDRREY (SEQ ID NO. 1), or a derivative of said peptide.

In another aspect, the present invention provides a peptide consisting of the amino acid sequence RLSVEI YDRREY (SEQ ID NO. 2), or a derivative of said peptide.

In another aspect, the invention provides a peptide comprising at least the amino acid sequence YDRLEY (SEQ ID NO. 20), or a derivative of said peptide.

In a related aspect, the invention provides a peptide as herein before described or a derivative thereof, including a cell membrane translocating motif. Preferably, said cell membrane translocating motif is peptide-based. More preferably, said cell membrane translocating motif is penetratin or a polymer of arginine.

In another aspect, the present invention provides isolated nucleic acids which encode a peptide or derivative thereof in accordance with the invention.

In a related aspect, the invention provides constructs or vectors comprising nucleic acids which encode a peptide or derivative thereof in accordance with the invention.

In a further aspect, the present invention provides a pharmaceutical composition comprising at least a peptide in accordance with the invention, or derivative thereof, together with one or more pharmaceutically acceptable diluents, carriers and/or excipients.

In a related aspect, the present invention provides a pharmaceutical composition comprising at least a nucleic acid or construct in accordance with the invention together with one or more pharmaceutically acceptable diluents, carriers and/or excipients.

In a further aspect of the present invention there is provided a method for modulating the function of integrin β7 in a subject comprising at least the step of administering to said subject an effective amount of a peptide, or derivative thereof, or composition comprising same as herein before described.

Alternatively, the method of modulating the function of integrin β7 in a subject comprises at least the step of administering to said subject an effective amount of a nucleic acid, construct, or composition comprising same as herein before described.

In a further aspect, the present invention provides a method of modulating the function of integrin β7 in an in vitro system the method comprising at least the step of administering to said system a peptide or derivative thereof, nucleic acid, construct, or composition in accordance with the invention.

In a further aspect of the invention there is provided a method for the treatment of integrin β7-mediated inflammatory disorders, the method comprising at least the step of administering to a subject in need thereof a therapeutically effective amount of a peptide, or derivative thereof, or composition comprising same as herein before described.

In a further aspect of the invention there is provided a method for the treatment of integrin β7-mediated inflammatory disorders, the method comprising at least the step of administering to a subject in need thereof a therapeutically effective amount of a nucleic acid, construct, or composition comprising said nucleic acid or construct as herein before described.

In another aspect, the present invention provides the use of a peptide or derivative thereof, or a nucleic acid or construct as herein before described in the manufacture of a medicament for the treatment of integrin β7-mediated inflammatory disorders.

In yet a further broad aspect, the present invention provides a method for the identification of potential β7 integrin functional interactors, or mimetics of the peptides of the invention, the method comprising at least the step of bringing a potential functional interactor or mimetic in contact with a peptide of the invention, or derivative thereof, and observing whether or not binding occurs.

In a related aspect of the invention the method further comprises the step of determining whether or not the functional interactor molecule or mimetic influences the level of adhesion of leukocytes to β7 integrin ligands. Preferably the method comprises the step of determining whether or not the functional interactor molecule or mimetic lowers the level of, or disrupts or prevents, adhesion of leukocytes to β7 integrin ligands.

In another aspect, the invention provides the use of a peptide or derivative thereof in accordance with the invention in identifying or screening for potential β7 integrin functional interactor molecules or mimetics of said peptides or derivatives thereof.

In a related aspect, the invention provides the use of a peptide or derivative thereof in accordance with the invention in designing mimetics of said peptide or derivative.

In another aspect, the invention provides an antibody directed against a peptide or derivative of the invention.

In another aspect, the invention provides a kit for modulating the function of integrin β7 or for the treatment of integrin β7-mediated inflammatory disorders, the kit comprising at least a peptide or derivative thereof in accordance with the invention.

In a related aspect, the invention provides a kit for modulating the function of integrin β7 or for the treatment of integrin β7-mediated inflammatory disorders, the kit comprising a nucleic acid or construct in accordance with the invention.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying figures, in which:

FIG. 1: Illustrates cell-permeable β7cyt peptide sequences, and their uptake by TK-1 T cells. (A) Peptides representing different regions of β7cyt (SEQ ID NO. 30) used in the study. Peptides were either fused to penetratin (Pen) (SEQ ID NO. 18) or a D-isomeric form of a nine amino acid arginine polymer (r9) (SEQ ID NO. 19). Upper and lowercase denote L- and D-enantiomers, respectively. The β3-CARD peptide containing the CARD from the integrin β3 subunit was used as a control. (B) Intracellular peptide was detected by staining fixed, permeabilized cytocentrifuged cell smears with FITC-streptavidin, followed by confocal laser scanning microscopy. The transverse sections of single cells presented are representative of 70-80% of the cell population. The panels illustrate cells that have taken up peptides β7-2 (B), β7-3 (C), β7-4 (D), β7-5 (E), β7-7 (F), β7-8 (G), β7-9 (H), and the β3-CARD (I). Panel A has cells only, and no peptide. The peptide sequence of β7-2 corresponds to that of SEQ ID NO. 2, while that of β7-8, β7-12, and β7-13 each correspond to SEQ ID NO. 1 (exclusive of the polymer of arginine and penetratin sequences). The peptide sequences of β7-3, β7-4, β7-5, β7-7, β7-9, β7-10, β7-11 and β3-CARD (excluding the polymer of arginine and penetratin sequences) have been allocated the sequence identifiers SEQ ID NO. 21 to SEQ ID NO. 28, in accordance with the sequence listing accompanying this specification.

FIG. 2: Illustrates that a cell-permeable peptide from the membrane-proximal region of β7cyt inhibits the adhesion of TK-1 cells to α4β7 ligands MAdCAM-1, VCAM-1, and RGD polymer. TK-1 cells were preincubated in the presence of increasing concentrations of peptides β7-2 to β7-5, activated with $Mn^{++}$ (A, D, F), PMA (B, E, G), and $AlF4^-$ (C), and added to glass slides coated with MAdCAM-1-Fc (A-C), VCAM-1-Fc (D, E), and fibronectin-like polymer (RGD) (F, G). Cells bound were counted, and represent the mean±SD from four fields. Experiments were performed in triplicate.

Figure 3A:
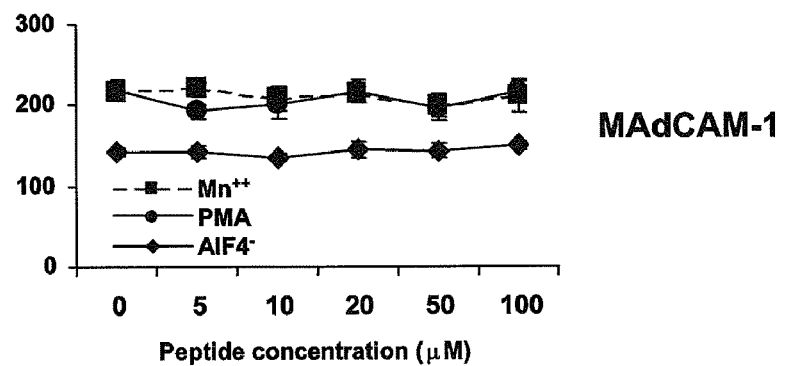
Figure 3B:
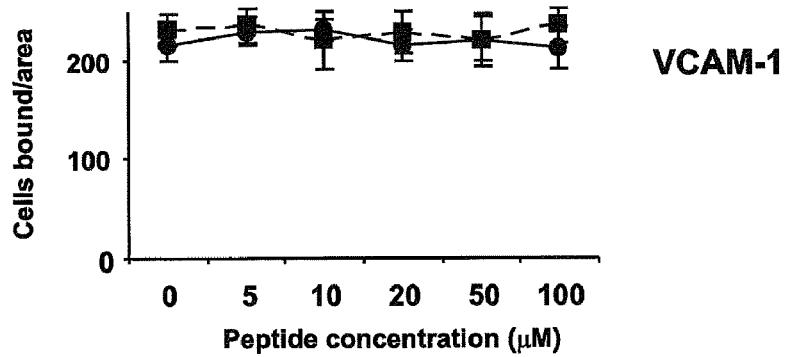
Figure 3C:
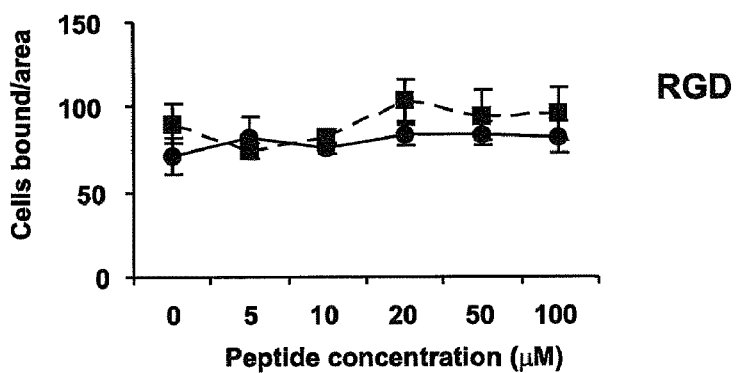

FIG. 3: Illustrates integrin α4β7-mediated cell adhesion is unaffected by the β3 subunit CARD. A cell-permeable peptide containing the CARD from the β3 subunit failed to inhibit the adhesion of $Mn^{++}$, PMA, and $AlF4^-$-activated TK-1 cells to MAdCAM-1 (A), VCAM-1 (B), and fibronectin-like polymer (RGD) (C). Cells bound were counted, and represent the mean±SD from four fields. Experiments were performed in triplicate.

FIG. 4: Illustrates the β7-2 peptide blocks cell adhesion across species, and is integrin-specific. Human H9 T cells were preincubated in the presence of increasing concentrations of peptides β7-2 to β-5, activated with $Mn^{++}$ (A, C), PMA (B, D), and added to glass slides coated with MAdCAM-1-Fc (A, B), and VCAM-1-Fc (C, D). Cells bound were counted, and represent the mean±SD from four fields. Experiments were performed in triplicate. (E) Inhibition of cell adhesion is integrin-specific. H9 T cells were preincubated in the presence of increasing concentrations of peptides β7-2 to β-5, activated with $Mn^{++}$, and added to glass slides coated with ICAM-1-Fc. Cells bound were counted, and represent the mean±SD from four fields. Experiments were performed in triplicate.

FIG. 5: Illustrates peptide β7-2 blocks ligand-induced clustering of α4β7 at the cell surface, but cannot disrupt established focal adhesions. (A) Peptide β7-2 blocks ligand-induced clustering of α4β7. TK-1 cells were preincubated with either the β7-2 or β7-3 peptides, or no peptide, and activated with $AlF4^-$. Ligand-induced clustering of α4β7 was induced by addition of MAdCAM-1-Fc, and cluster formation after 30 min was determined by staining cells with FITC-conjugated M293 mAb (anti-β7 subunit), followed by confocal microscopy. Each panel shows transverse (left quandrants) and surface (right quadrants) views of either a single cell (upper quadrants) at high magnification, or a population of cells (lower quadrants) at lower magnification. B-E) Peptide β7-2 cannot disrupt focal adhesions to detach cells. TK-1 (B, D) and H9 (C, E) cells activated with $Mn^{++}$, and PMA were adhered to glass slides coated with MAdCAM-1-Fc (B, C), and VCAM-1-Fc (D, E), and then incubated for 1 h with peptide β7-2. Cells bound were counted, and represent the mean±SD from four fields. Experiments were performed in triplicate.

Figures 6A, 6B, 6C, 6D, 6E, 6F, 6G:
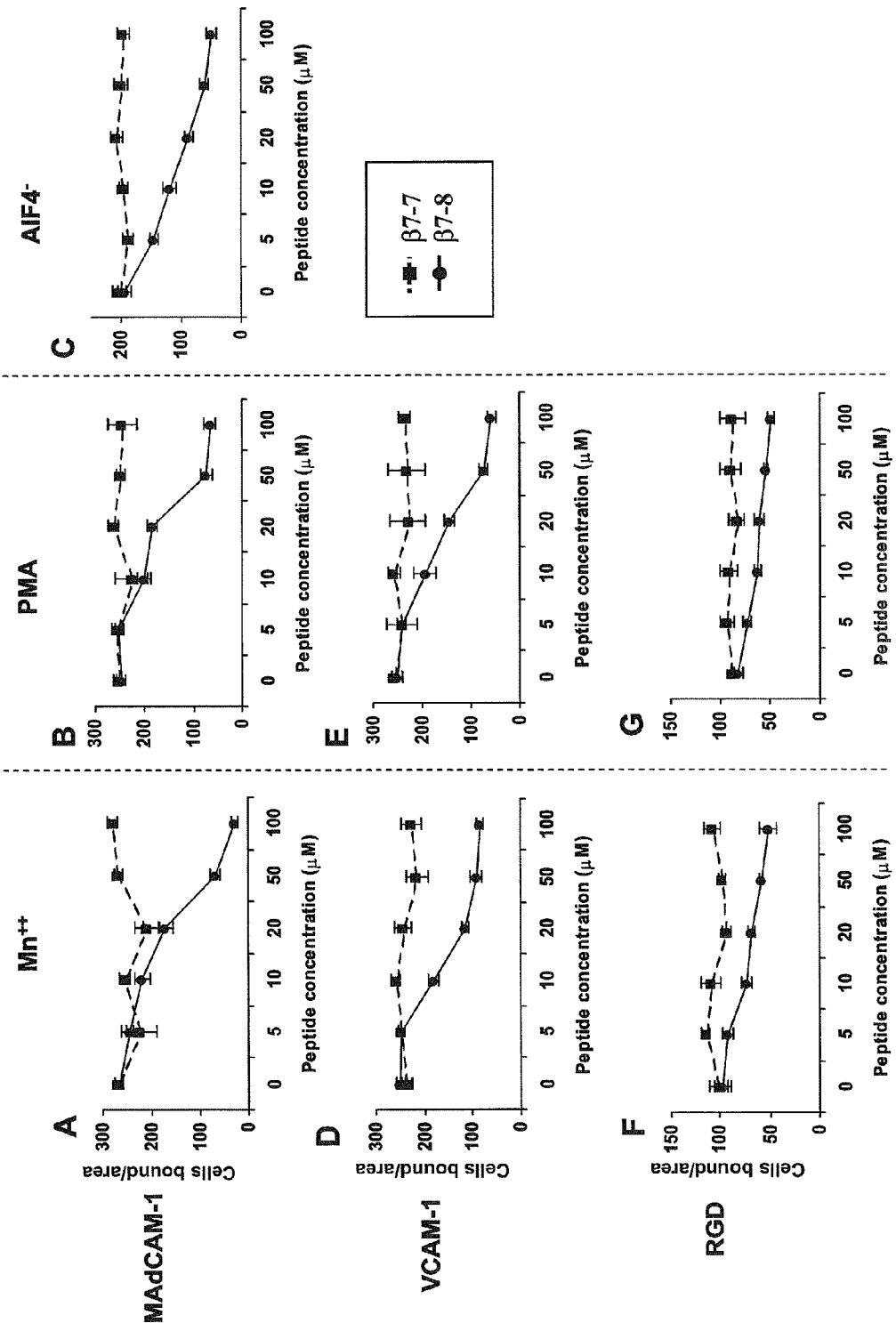

FIG. 6: Illustrates a six amino acid CARD motif exists within peptide β7-2. The β7-2 peptide was divided into two to give peptides β7-7 and β7-8. TK-1 cells were preincubated in the presence of increasing concentrations of peptides β7-7 and β7-8, activated with $Mn^{++}$ (A, D, F), PMA (B, E, G), and $AlF4^-$ (C), and added to glass slides coated with MAdCAM-1-Fc (A-C), VCAM-1-Fc (D, E), and fibronectin-like polymer (F, G). Cells bound were counted, and represent the mean±SD from four fields. Experiments were performed in triplicate.

FIG. 7: Illustrates tandem tyrosines are critical for the activity of the β7 CARD. TK-1 cells were preincubated in the presence of increasing concentrations of peptide β7-8, and a mutant peptide, β7-9, in which tyrosines 735 and 740 had been substituted with phenylalanines. Cells were activated with $Mn^{++}$ (A, D), PMA (B, E), and $AlF4^-$ (C), and added to glass slides coated with MAdCAM-1-Fc (A-C), and VCAM-1-Fc (D, E). Cells bound were counted, and represent the mean±SD from four fields. Experiments were performed in triplicate. Similar results were obtained for H9 cells.

Figure 8:
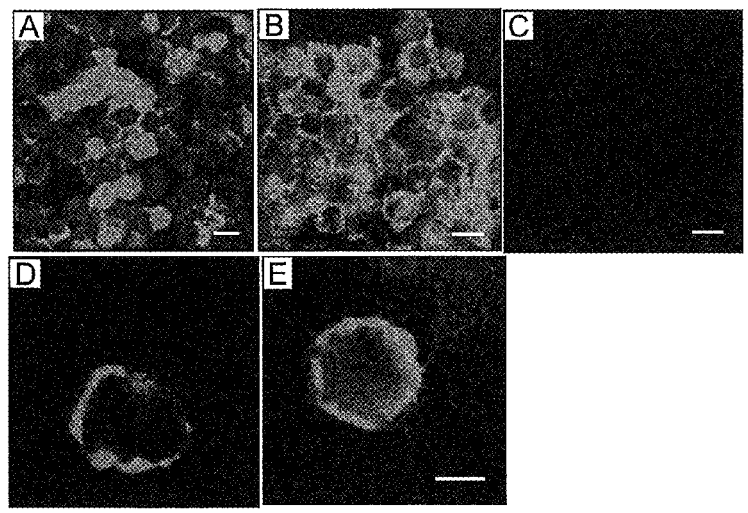
Figure 8:
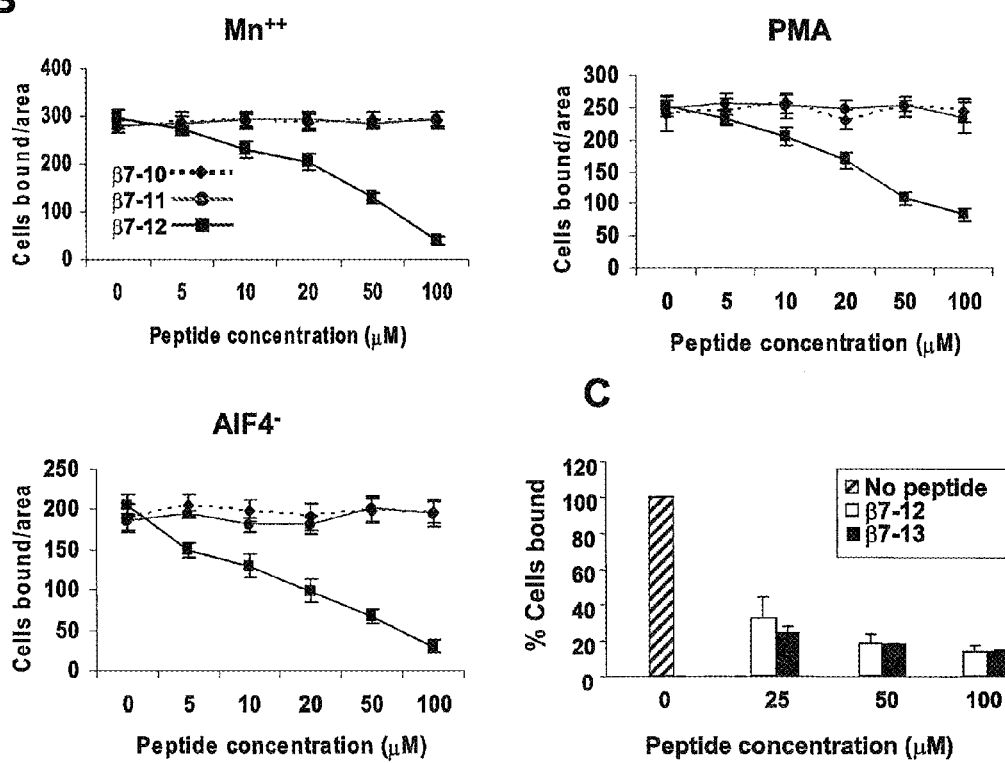
Figure 8:
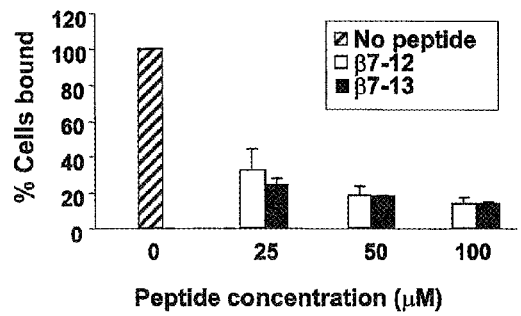

FIG. 8: Illustrates tyrosines 735 and 740 are both essential for β7 CARD activity. (A) Confocal images showing internalisation by TK-1 cells of variant forms of the β7 CARD (YDRREY (SEQ ID NO. 1)) fused to a biotinylated R9 peptide. Intracellular peptide was detected (stained green) after a 30 min incubation as described in FIG. 1B. Panels illustrate cells that have internalized an L-amino acid form of the β7 CARD (peptide β7-12) (A,D), and a D-amino acid form of the β7 CARD (peptide β7-13) (B,E). Panel C illustrates cells without peptide. Bar; panels A-C, 10 μm, panels D and E, 5 μm. (B) TK-1 cells were preincubated in the presence of increasing concentrations of peptide β7-12, and mutant peptides β7-10, and β7-11, in which tyrosines 735 and 740 had been individually deleted, respectively. Cells were activated with $Mn^{++}$, PMA, and $AlF4^-$, as indicated, and added to glass slides coated with MAdCAM-1-Fc. Cells bound were counted, and represent the mean±SD from four fields. Experiments were performed in triplicate. (C) A D-amino acid analogue of the β7 CARD retains activity. Both L (β7-12) and D (β7-13) amino acid analogs of YDRREY (SEQ ID NO. 1) fused to a biotinylated R9 peptide inhibit the adhesion of CMFDA-labeled murine TK-1 cells to human VCAM-1 Fc. Data represent the means±SD from two independent experiments performed in duplicate.

Figure 9:
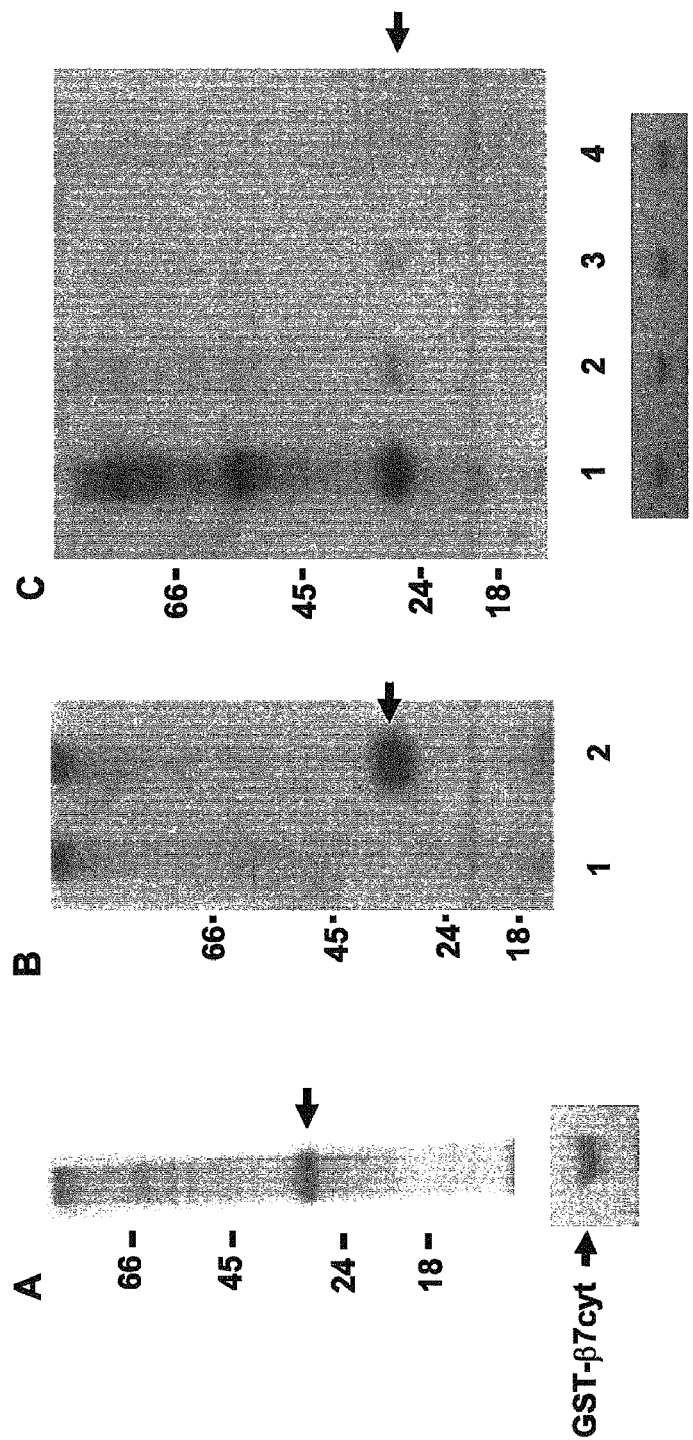

FIG. 9: Illustrates tyrosines 735 and 740 in the β7 CARD are both phosphorylatable. (A) The β7 cytoplasmic domain is strongly tyrosine phosphorylatable. (Upper panel) A GST fusion protein containing the cytoplasmic domain of the human β7 subunit was immobilized on Sepharose and subjected to an in vitro kinase assay with trace amounts of an H9 cell lysate (1:100 dilution). The GST-fusion protein (arrowed) was resolved on a 10% polyacrylamide SDS gel that was subsequently treated with 1M KOH, and exposed to X-ray film. The sizes in kDa of molecular weight markers are given in the left-hand margin. (Lower panel) The GST-fusion protein was stained with Coomassie blue. (B) The phosphorylated GST-β7cyt fusion protein in (A) was removed from Sepharose beads by boiling the beads in SDS. The sample was diluted, and subjected to immunoprecipitation with either normal rabbit serum (lane 1) or a polyclonal rabbit anti-β7cyt antibody (lane 2). Immunoprecipitates were resolved by SDS-PAGE, as above. (C) The β7 cytoplasmic domain is specifically phosphorylated on tyrosine. (Upper panel) A GST-β7cyt fusion protein immobilized on Sepharose was subjected to an in vitro kinase assay with trace amounts of an H9 cell lysate (1:100 dilution) in the absence (lane 1) or presence of 5 (lane 2), 10 (lane 3), and 20 (lane 4) μM genistein. The GST-fusion protein was resolved on a 10% polyacrylamide SDS gel, and exposed to X-ray film. The sizes in kDa of molecular weight markers are given in the left-hand margin. (Lower panel) The GST-fusion protein was stained with Coomassie blue. (D) The two tyrosine residues in the YDRREY (SEQ ID NO. 1) motif are phosphorylatable. Biotinylated peptides β7-3, β7-4, β7-7, β7-8, β7-10, and β7-11 were immobilized on streptavidin-Sepharose, and subjected to an in vitro kinase assay with lysates of TK-1 cells that had been either activated with $AlF4^-$ (filled bars) or left unactivated (empty bars). Each experiment was done in triplicate, and the results represent the mean cpm+SD.

FIG. 10: Illustrates the sequence of human and mouse β7cyt, and comparison with the cytoplasmic domains of other integrin β subunits. The positions of the β3 and β7 CARDs, and residues in the CARD that are shared with other β integrin tails are highlighted. Tyrosine phosphorylation sites in β7cyt are underlined. Residues that are common to several β integrin tails are emboldened. M, mouse; H, human. The peptide sequences β7 M, β7 H, β6, β5, β3, β2, and β1 have been allocated the sequence identifiers SEQ ID NO. 29 to SEQ ID NO. 35, in accordance with the sequence listing accompanying this specification.

PREFERRED EMBODIMENT(S)

The following is a description of the present invention, including preferred embodiments thereof, given in general terms. The invention is further elucidated from the disclosure given under the section entitled "Examples" herein after, which provides experimental support for, and specific examples of, the invention.

The inventors of the present invention have identified a regulatory motif within the β7 integrin subunit. This motif, YDRREY (SEQ ID NO. 1), encompasses residues 735-740 of the transmembrane-proximal region of the cytoplasmic tail of the β7. While not wishing to be bound by any particular theory, the inventors propose that this phosphorylatable motif constitutes a major cell adhesion regulatory domain (CARD) that modulates the interaction of β7-expressing leukocytes with their extracellular matrix, endothelial and epithelial cells, dendritic cells and other cells expressing appropriate ligands.

The inventors have surprisingly found that peptides comprising at least the motif YDRREY (SEQ ID NO. 1) are able to disrupt the interaction of β7 integrins with their ligands, for example MAdCAM-1 and VCAM-1. This action has been demonstrated across species, namely mice and humans. The implication is that peptides of the invention compete for intracellular proteins or factors that are critical in controlling the function of β7 integrins thereby modulating their cellular adhesion function.

On the basis of the above findings, a peptide of the invention, or a pharmaceutical composition comprising same, may be used to modulate the cellular adhesion function of β7 integrins, particularly the adhesion of leukocytes to each other, to the extracellular matrix and to epithelial and endothelial cells, both in in vitro systems and in vivo. Such modulation has application in controlling β7 integrin-mediated inflammatory events, and particularly in the treatment of β7 integrin-mediated inflammatory disorders.

Similarly, the inventors contemplate the use of nucleic acids encoding peptides of the invention, and constructs or vectors comprising such nucleic acids, in methods for modulating the cellular adhesion function of β7 integrins, likewise including treatment of β7 integrin-mediated inflammatory disorders.

Additionally, a peptide of the invention may be used in assays for the identification of β7 integrin functional interactor molecules which may bind to and/or regulate the function of β7 integrins. As used herein the term "β7 integrin functional interactors" should be taken in its broadest context. It is intended to include molecules such as intracellular signalling molecules and other cellular components which may modulate the cellular adhesion function of the β7 integrins, and also potential therapeutic agents which may have application in treatment of disorders mediated by this function.

Furthermore, peptides of the invention may be used in assays to specifically identify interference molecules directed against the cytoplasmic domain of the integrin β7 subunit. As used herein, "interference molecules" are those molecules which are adapted to bind to a region of the cytoplasmic domain of the integrin subunit including a peptide motif of the invention. Preferably such "interference molecules" block the interaction of at least a region of the cytoplasmic domain with other molecules, and more preferably block the function of cytoplasmic domain of the integrin subunit. "Interference molecules" include, but are not limited to, antibodies and nucleic acid aptamers (for example, RNA and DNA aptamers).

"Interference molecules" may find use in modulating or inhibiting the activity and function of β7 integrins, including disrupting or preventing the interaction of β7 integrins with their ligands, for example MAdCAM-1 and VCAM-1, thus modulating the cellular adhesion function of the β7 integrins, and having application in controlling β7 integrin-mediated inflammatory events, and particularly in the treatment of β7 integrin-mediated inflammatory disorders.

Peptides of the invention may also be used to design mimetics, including small molecule mimetics, or to screen libraries for such suitable mimetics of the peptides, which may be of use therapeutically.

The phrases "modulate adhesion of leukocytes to each other and to epithelial and endothelial cells", "modulating the cellular adhesion function of β7 integrins" or "regulate the function of β7 integrins", and the like, are generally used herein to refer to down-regulation of function. However, the inventors contemplate situations where up-regulation of function of the β7 integrins may occur through use of peptides, nucleic acids, or constructs of the invention; for example, where the peptides competitively bind to functional interactors which may have a negative effect on β7 integrin function. Accordingly, up-regulation of function of the β7 integrins is also encompassed by the present invention. To this end, while pharmaceutical compositions and methods are described herein after in relation to the treatment of inflammatory disorders, which implies down-regulation of β7 integrin function, it should be understood that they may equally be applicable to treatments where up-regulation of β7 integrin function is desirable.

The term "inflammatory disorder(s)" should be taken to mean any undesired physiological condition which involves inflammation, aberrant or otherwise. "Inflammation" should be broadly taken to mean a characteristic reaction of tissues to injury or disease, or foreign particles and noxious stimuli, resulting in one or more of redness, swelling, heat, and pain. In accordance with the present invention, such inflammatory disorders will be mediated by the action of β7 integrins, and include, but are not limited to, demyelinating diseases such as multiple sclerosis, Type I diabetes mellitus, inflammatory bowel disease, asthma, arthritis, gastritis, mucositis, graft-versus-host disease, hepatitis, psoriasis, Graves disease, septic shock, hemorrhagic shock, ischemica-reperfusion injury, arterial/vascular injury, transplant rejection, and inflammation that impedes tissue/skin healing.

As used herein, the term "treatment" is to be considered in its broadest context. The term does not necessarily imply that subject is treated until total recovery. Accordingly, "treatment" broadly includes the modulation or control of inflammation, or other β7 integrin-mediated event, aberrant or otherwise, amelioration of the symptoms or severity of a particular disorder, or preventing or otherwise reducing the risk of developing a particular disorder.

It will be appreciated by those of general skill in the art to which the invention relates, having regard to the nature of the invention and the results reported herein, that the present invention is applicable to a variety of different animals. Accordingly, a "subject" includes any animal of interest. In particular the invention is applicable to mammals, more particularly humans.

It should be understood that a peptide or protein in accordance with the invention, is an "isolated" or "purified" peptide or protein. An "isolated" or "purified" peptide or protein is one which has been identified and separated from the environment in which it naturally resides. It should be appreciated that 'isolated' does not reflect the extent to which the peptide has been purified or separated from the environment in which it naturally resides. Peptides of use in the invention may be purified from natural sources, or derived by chemical synthesis or recombinant techniques.

It should be understood that a nucleic acid in accordance with the invention, is an "isolated" or "purified" nucleic acid. An "isolated" or "purified" nucleic is one which has been identified and separated from the environment in which it naturally resides. It should be appreciated that 'isolated' does not reflect the extent to which the nucleic has been purified or separated from the environment in which it naturally resides. Nucleic acids of use in accordance with the invention may be purified from natural sources, or derived by chemical synthesis or recombinant techniques.

Peptides and Derivatives Thereof

In a particularly preferred embodiment a peptide of the invention comprises the amino acid sequence YDRREY (SEQ ID NO. 1). While the peptide may consist solely of the motif YDRREY (SEQ ID NO. 1), it should be appreciated that larger peptides in which the motif YDRREY (SEQ ID NO. 1) is incorporated are also encompassed by the present invention. By way of example, the core motif YDRREY (SEQ ID NO. 1) may be extended at either or both of its N-terminus or C-terminus by additional amino acids, for example 1 to 6 amino acids, taken from the native β7 subunit amino acid sequence at the relevant position. Exemplary β7 sequence information is found in GenBank, see accession numbers NM_000889 (human), NM_013566 (mouse), and XM_343336 (rat). Consistent with this, the peptide β7-2 comprising amino acids RLSVEIYDRREY (SEQ ID NO. 2), as described further herein after, forms part of the present invention. Alternatively, the core motif may be extended by, or fused to, heterologous amino acid motifs or sequences where desired. In this regard, a peptide of the invention should be taken to include fusion peptides or proteins.

It should be appreciated that a "peptide" according to the invention extends to any peptide that has been fused with, conjugated to, or otherwise incorporates, a motif which renders it cell-permeable. The motif may allow for active or passive movement of the peptide across or through the cell membrane. The motif may be referred to herein as a cell membrane translocating motif. Such a motif is preferably a peptide-based membrane translocating motif. However, those of skill in the art to which the invention relates will readily recognise motifs of an alternative nature which may effectively provide cell-permeability; for example, motifs that are bound by and internalized by cell-surface receptors, or lipid moieties. The Chariot transfection reagent is designed to transmit biologically active proteins and peptides into living cells, for example.

A peptide-based membrane translocating motif in accordance with the invention will effectively render a peptide cell-permeable, whilst retaining at least a degree of the desired function of said peptide. Those of skill in the art to which the present invention relates will readily appreciate peptide-based membrane translocating motifs of use in the invention. However, the inventors have found penetratin and a polymer of arginine (as detailed herein after under the heading "Examples") to be of particular use. Further suitable peptide-based membrane translocating motifs are described in the review by Joliot and Prochiantz-Transduction peptides: from technology to physiology. Nat Cell Biol. 2004; 6(3): 189-96 (e.g., Tat RKKRRQRRR (SEQ ID NO. 3), Buforin II TRSSRAGLQFPVGRVHRLLRK (SEQ ID NO. 4), Transportan GWTLNSAGYLLGKINKALAALAKKIL (SEQ ID NO. 5), MAP (model amphipathic peptide) KLALKLAL-KALKAALKLA (SEQ ID NO. 6), K-FGF AAVALLPAVL-LALLAP (SEQ ID NO. 7), Ku70 VPMLK (SEQ ID NO. 8) or PMLKE (SEQ ID NO. 9), Prion MANLGYWLLALFVTM-WTDVGLCKKRPKP (SEQ ID NO. 10), pVEC LLIILRRR-IRKQAHAHSK (SEQ ID NO. 11), Pep-1 KETWWETWW-TEWSQPKKKRKV (SEQ ID NO. 12), SynB1 RGGRLSYSRRRFSTSTGR (SEQ ID NO. 13), Pep-7 SDL-WEMMMVSLACQY (SEQ ID NO. 14), HN-1 TSPLNIH-NGQKL (SEQ ID NO. 15).

A peptide of the invention may be composed of L-amino acids, D-amino acids or a mixture thereof.

The core YDRREY (SEQ ID NO. 1) amino acid sequence may be modified by substitution of one or more of the amino acids of the core DRRE (SEQ ID NO. 37) sequence with alternative amino acids, provided the modified peptide retains at least a degree of the desired function of the peptide YDRREY (SEQ ID NO. 1). In one embodiment of the invention the amino acid substitution is conservative. Persons skilled in the art will appreciate appropriate conservative amino acid substitutions based on the relative similarity between different amino acids, including the similarity of the amino-acid side chain substituents (for example, their size, charge, hydrophilicity, hydrophobicity and the like). However by way of example, D may be replaced with E, R may be replaced with K, and E may be replaced with D. In another embodiment the amino acid substitution is non-conservative. Persons of skill in the art will appreciate such non-conservative substitutions. However, by way of example, R could be replaced with L.

In one particular embodiment of the invention one of the R residues, particularly the second R residue, within the peptide is substituted by another amino acid. The inventors note that the rat amino acid sequence corresponding to YDRREY (SEQ ID NO. 1), is YDRLEY (SEQ ID NO. 20). Accordingly the inventors contemplate that at least the second R residue is not essential to function.

The inventors also contemplate shortening of a peptide of the invention, by deletion of amino acids within the DRRE (SEQ ID NO. 37) core sequence, provided such shortened peptides retain at least a degree of the desired function of the peptide YDRREY (SEQ ID NO. 1).

"Peptides" of the invention may be chemically modified where desirable. For example peptides may be modified by acetylation, glycosylation, cross-linking, disulfide bond formation, cyclization, branching, phosphorylation, conjugation or attachment to a desirable molecule (for example conjugation to bispecific antibodies), acylation, ADP-ribosylation, amidation, covalent attachment of a lipid or lipid derivative, covalent attachment of phosphotidylinositol, demethylation, formation of covalent cross-links, formation of cysteine, formation of pyroglutamate, formylation, gamma-carboxylation, GPI anchor formation, hydroxylation, methylation, myristoylation, oxidation, pegylation, proteolytic processing, prenylation, racemization, conversion from L-isomer to D-isomer, sulfation, or otherwise to mimic natural post-translational modifications, for example. The peptides may also be modified to include one or more non-naturally occurring amino acids, as will be known in the art. Amino acids of a peptide may also be modified by substitution of R groups for other chemical groups as may be known in the art. In addition, amino acids may be substituted with chemical groups which mimic them; for example, benzimidazole is a known mimic of R and 1,4-benzodiazepine a mimic of G-D (see Curr Protein Pept Sci 2005 April; 6(2):151-169. Peptides of the invention may also be modified by arrangement of amino acid groupings from the peptide on a non-peptide scaffold. Considerations for designing such modified peptides are discussed in Curr Protein Pept Sci. 2005 April; 6(2):151-169 (Sillerud and Larson).

The invention should be taken to include pharmaceutically acceptable salts of peptides as well as stereoisomers of peptides. Persons of skill in the art will appreciate such salts and stereoisomers.

Peptides of the invention which have been modified as described herein before (for example, by chemical modification, addition of side groups, addition/inclusion of a cell membrane translocating motif, addition of further amino acids (including heterologous amino acids), inclusion of non-naturally occurring amino acids, substitution of amino acids, substitution of amino acid R groups, salts, isomers, reduction to peptidomimetics, and the like), or by other means known in the art, may be referred to herein as "derivatives" of the peptides.

Use herein of the words "peptide" or "peptides" should be taken to include reference to "derivatives" of such peptides, unless the context requires otherwise. In addition, "peptides" and "derivatives" thereof should be taken to include "prodrugs", that is peptides or derivatives which are in an inactive form and which are converted to an active form by biological conversion following administration to a subject.

"Derivatives" of the peptides of the invention will retain at least a degree of the desired function of said peptides; that is the ability to modulate the function of β7 integrins (as described herein) and preferably down-regulate, lower or inhibit function. Accordingly, an alternative term for "derivatives" may be "functional derivatives". The function of a derivative can be assessed, for example, using in vitro cell adhesion assays as described in the "Examples" section herein after. Skilled persons may readily appreciate alternative assays, including in vivo assays in animals.

A peptide of the invention may be purified from natural sources, or preferably derived by chemical synthesis (for example, fmoc solid phase peptide synthesis as described in Fields G B, Lauer-Fields J L, Liu R Q and Barany G (2002) Principles and Practice of Solid-Phase peptide Synthesis; Grant G (2002) Evaluation of the Synthetic Product. Synthetic Peptides, A User's Guide, Grant G A, Second Edition, 93-219; 220-291, Oxford University Press, New York) or genetic expression techniques (as are outlined broadly herein after), methods for which are readily known in the art to which the invention relates. The inventor's contemplate production of a peptide of the invention by an appropriate transgenic animal, microbe, or plant.

To the extent that a peptide of the present invention may be produced by recombinant techniques the invention provides nucleic acids encoding peptides of the invention and constructs or vectors which may aid in the cloning and expression of such nucleic acids. Certain such constructs may also be of use to a therapeutic end as herein after detailed.

Those of general skill in the art to which the invention relates will readily be able to identify nucleic acids which encode peptides of the invention, including desired fusion peptides or proteins, on the basis of the amino acid sequences of the desired peptides, sequence information contained herein, the genetic code, and the understood degeneracy therein. However, by way of example: CGG CTC TCG GTG GAA ATC TAT GAC CGC CGG GAA TAC (SEQ ID NO. 16) for a peptide having the amino acid sequence RLSVEI YDRREY (SEQ ID NO. 2) and TAT GAC CGC CGG GAA TAC (SEQ ID NO. 17) for a peptide having the amino acid sequence YDRREY (SEQ ID NO. 1), are appropriate nucleic acids.

Nucleic acid constructs in accordance with this embodiment of the invention will generally contain heterologous nucleic acid sequences; that is nucleic acid sequences that are not naturally found adjacent to the nucleic acid sequences of the invention. The constructs or vectors may be either RNA or DNA, either prokaryotic or eukaryotic, and typically are viruses or a plasmid. Suitable constructs are preferably adapted to deliver a nucleic acid of the invention into a host cell and are either capable or not capable of replicating in such cell. Recombinant constructs comprising nucleic acids of the invention may be used, for example, in the cloning, sequencing, and expression of nucleic acid sequences of the invention. Additionally, as is herein after detailed, recombinant constructs or vectors of the invention may be used to a therapeutic end.

Those of skill in the art to which the invention relates will recognise many constructs suitable for use in the present invention. However, the inventors contemplate the use of cloning vectors such as pUC and pBluescript and expression vectors such as pCDM8, adeno-associated virus (AAV) or lentiviruses to be particularly useful; exemplification in regard to cloning and expression vectors is also provided herein under the heading "Examples".

The constructs may contain regulatory sequences such as promoters, operators, repressors, enhancers, termination sequences, origins of replication, and other appropriate regulatory sequences as are known in the art. Further, they may contain secretory sequences to enable an expressed protein to be secreted from its host cell. In addition, expression constructs may contain fusion sequences (such as those that encode a heterologous amino acid motif, for example penetratin, mentioned herein before) which lead to the expression of inserted nucleic acid sequences of the invention as fusion proteins or peptides.

In accordance with the invention, transformation of a construct into a host cell can be accomplished by any method by which a nucleic acid sequence can be inserted into a cell. For example, transformation techniques include transfection, electroporation, microinjection, lipofection, adsorption, and biolistic bombardment.

As will be appreciated, transformed nucleic acid sequences of the invention may remain extrachromosomal or can integrate into one or more sites within a chromosome of a host cell in such a manner that their ability to be expressed is retained.

Any number of host cells known in the art may be utilised in cloning and expressing nucleic acid sequences of the invention. For example, these include but are not limited to microorganisms such as bacteria transformed with recombinant bacteriophage DNA, plasmid DNA or cosmid DNA expression vectors; yeast transformed with recombinant yeast expression vectors; insect cell systems infected with recombinant virus expression vectors (e.g., baculovirus); animal cell systems such as CHO (Chinese hamster ovary) cells using the pEE14 plasmid system; plant cell systems infected with recombinant virus expression vectors (e.g., cauliflower mosaic virus, CaMV; tobacco mosaic virus, TMV) or transformed with recombinant plasmid expression vectors (e.g., Ti plasmid). Those host cells detailed herein after under "Examples" are found to be particularly useful.

A recombinant peptide in accordance with the invention may be recovered from a transformed host cell, or culture media, following expression thereof using a variety of techniques standard in the art. For example, detergent extraction, sonication, lysis, osmotic shock treatment and inclusion body purification. The protein may be further purified using techniques such as affinity chromatography, ion exchange chromatography, filtration, electrophoresis, hydrophobic interaction chromatography, gel filtration chromatography, and chromatofocusing.

As mentioned herein before, a peptide of the invention may be in the form of a fusion peptide or protein; for example, a peptide of the invention attached to a peptide-based membrane translocating motif, or alternatively, or in addition, a motif which may aid in subsequent isolation and purification of the peptide (for example, ubiquitin, his-tag, or biotin). Means for generating such fusion peptides are readily known in the art to which the invention relates, and include chemical synthesis and techniques in which fusion peptides are expressed in recombinant host cells, as mentioned herein before. The inventors contemplate Strep-tag (Sigma-Genosys), Impact™ system (New England Biolabs), his-tag, and the eg pMAL™-p2 expression system (New England BioLabs), to be particularly useful in the present instance. Further exemplification is provided herein after under "Examples". In addition, fusion tags of use in recombinant protein expression and purification have been described by R. C. Stevens. "Design of high-throughput methods of protein production for structural biology" Structure, 8, R177-R185 (2000).

Membrane translocating motifs may also be fused, conjugated or otherwise incorporated in or attached to a peptide by alternative means known in the art to which the invention relates. For example, where cell-permeabilising moieties comprise an entire protein, fatty acids and/or bile acids, such molecules may be linked to the active peptide by an amino acid bridge, or by a non-peptidyl linkage.

A peptide of the invention, for example YDRREY (SEQ ID NO. 1), may be simultaneously joined to two tags, where one tag allows for cell secretion (e.g., signal peptide), and another tag renders the peptide cell-permeable. In this scenario the peptide could be produced and secreted by a non-leukocyte to be subsequently taken up by a leukocyte. This could be advantageous for instance where one may wish parenchymal or endothelial cells within an inflamed tissue to secrete the peptide to inhibit the adhesion of infiltrating leukocytes.

Compositions and Methods of Treatment

Inasmuch as the present invention relates to the modulation of integrin β7 function, including the treatment of inflammatory disorders, it also provides a pharmaceutical composition comprising a peptide of the invention, or a derivative thereof, in association with one or more pharmaceutically acceptable diluents, carriers and/or excipients.

The invention also provides a pharmaceutical composition comprising a nucleic acid encoding a peptide of the invention, or construct comprising same, in association with one or more pharmaceutically acceptable diluents, carriers and/or excipients.

As-used herein, the phrase "pharmaceutically acceptable diluents, carriers and/or excipients" is intended to include substances that are useful in preparing a pharmaceutical composition, may be co-administered with an appropriate agent for example a peptide, nucleic acid encoding said peptide, or construct comprising same, of the invention while allowing the agent to perform its intended function, and are generally safe, non-toxic and neither biologically nor otherwise undesirable. Pharmaceutically acceptable diluents, carriers and/or excipients include those suitable for veterinary use as well as human pharmaceutical use. Examples of pharmaceutically acceptable diluents, carriers and/or excipients include solutions, solvents, dispersion media, delay agents, emulsions and the like.

In addition to standard diluents, carriers and/or excipients, a pharmaceutical composition in accordance with the invention may be formulated with additional constituents, or in such a manner, so as to enhance the activity of a peptide, or nucleic acid or construct of the invention, or help protect the integrity of such agents. For example, the composition may further comprise constituents which provide protection against proteolytic degradation, enhance bioavailability, decrease antigenicity, or enable slow release upon administration to a subject. For example, slow release vehicles include macromers, poly(ethylene glycol), hyaluronic acid, poly(vinylpyrrolidone), or a hydrogel.

Furthermore, cell permeability of a peptide, derivative thereof, or nucleic acid or construct of the invention may be achieved, or facilitated, through formulation of the composition.

Additionally, it is contemplated that a pharmaceutical composition in accordance with the invention may be formulated with additional active ingredients which may be of benefit to a subject in particular instances. Persons of ordinary skill in the art to which the invention relates will readily appreciate suitable additional active ingredients having regard to the description of the invention herein and the nature of a particular disorder to be treated, for example. As a general example, antibodies, small molecule inhibitors, immunosuppressors, pharmaceutical drugs (e.g., steroids), may be used.

In one embodiment, the present invention also pertains to methods for the treatment of inflammatory disorders comprising at least the step of administering to a subject in need thereof a therapeutically effective amount of a peptide of the invention, or a pharmaceutical composition comprising same. In a related embodiment the method involves the administration to a subject in need thereof of a therapeutically effective amount of a nucleic acid encoding a peptide of the invention, or a construct comprising same.

It should be appreciated that peptides (and derivative thereof) of the invention may be administered and formulated as pro-drugs, which are converted to active agents following administration.

As used herein, a "therapeutically effective amount", or an "effective amount" is an amount necessary to at least partly attain a desired response.

The inventors contemplate administration of a peptide, derivative thereof, nucleic acid encoding a peptide of the invention, or a construct comprising same, or pharmaceutical compositions of any one or more of these agents by any means capable of delivering such agents to leukocytes at a target site within the body of a subject; a "target site" is a site at which an inflammatory event has, or is predicted to, occur, or a site which may otherwise benefit from the delivery of said peptide. By way of example, compounds of this invention may be administered as pharmaceutical compositions by one of the following routes: oral, topical, systemic (eg. transdermal, intranasal, or by suppository), parenteral (eg. intramuscular, subcutaneous, or intravenous injection), by administration to the CNS (eg. by intraspinal or intracisternal injection); by implantation, and by infusion through such devices as osmotic pumps, transdermal patches, and the like. Further examples may be provided herein after. Skilled persons may identify other appropriate administration routes.

In accordance with such modes of administration, and the suitable pharmaceutical excipients, diluents and/or carriers mentioned herein before, compositions of the invention may be converted to customary dosage forms such as solutions, orally administrable liquids, injectable liquids, tablets, coated tablets, capsules, pills, granules, suppositories, trans-dermal patches, suspensions, emulsions, sustained release formulations, gels, aerosols, powders and immunoliposomes. Additionally, sustained release formulations may be utilised. The dosage form chosen will reflect the mode of administration desired to be used. Particularly preferred dosage forms include orally administrable tablets, gels, pills, capsules, semisolids, powders, sustained release formulation, suspensions, elixirs, aerosols, ointments or solutions for topical administration, and injectable liquids. Further specific examples will be provided herein after.

As will be appreciated, the dose of an agent or composition administered, the period of administration, and the general administration regime may differ between subjects depending on such variables as the severity of symptoms of a subject, the type of disorder to be treated, the mode of administration chosen, and the age, sex and/or general health of a subject.

Data obtained from cell culture assays and animal studies can be used in formulating a range of dosages for use in humans. The dosage may vary within this range depending upon the dosage form employed and the route of administration utilized. For any compound used in the method of the invention, the therapeutically effective dose can be estimated initially from cell culture assays. A dose may be formulated in cell cultures or animal models to achieve a cellular concentration range that includes the IC50 (i.e., the concentration of the test compound that achieves a half-maximal inhibition of symptoms) as determined in cell culture. Such information can be used to more accurately determine useful doses in humans. The exact formulation, route of administration and dosage can be chosen by the individual physician in view of the patient's condition. (See, e.g., Fingl et al., 1975, In: The Pharmacological Basis of Therapeutics, Ch. 1, p. 1).

Specific examples of compositions and modes of administration relevant to 1) peptides, and 2) nucleic acids are now provided. These are given by way of example only.

Peptide Compositions and Modes of Administration

Those skilled in the art of peptide-based treatments will readily appreciate a variety of pharmaceutically acceptable diluents, carriers and/or excipients which may be employed in compositions of the invention comprising one or more peptides. By way of example, suitable liquid carriers, especially for injectable solutions, include water, aqueous saline solution, aqueous dextrose solution, and the like, with isotonic solutions being preferred for intravenous, intraspinal, and intracisternal administration. Diluents, carriers and/or excipients may be chosen to enhance peptide stability. For example, one or more of the following may be used: buffer(s), blocking agent(s), solvent(s), salt(s), chelator(s), detergent(s), and preservative(s). Stabilizing diluents for polypeptides and antigens are described for example in U.S. Pat. No. 6,579,688.

As mentioned herein before, peptides of the invention may be formulated to allow for slow release. Pharmaceutical compositions for prolonged peptide release and preparation method are described for example in U.S. Pat. Nos. 6,503,534 and 6,482,435, and 6,187,330, and 6,011,011. In addition, to prolong the in vivo half-life of proteins and to reduce their antigenicity proteins may be conjugated to soluble synthetic polymers, in particular poly(ethylene glycol), poly(vinyl pyrrolidone), poly(vinyl alcohol), poly(amino acids), divinylether maleic anhydride, ethylene-maleic anhydride, N-(2-hydroxypropyl)methacrylamide and dextran. Methods for synthesis of polymer bio-active conjugates are described for example in U.S. Pat. No. 6,172,202. Peptides may also be delivered via implants as described in U.S. Pat. No. 6,077,523.

Furthermore, while a peptide of the invention may be rendered cell-permeable by fusion or conjugation to an appropriate membrane translocating motif, cell permeability may alternatively be achieved, or further be facilitated, through formulation of the composition. Pharmaceutical formulation of a therapeutic polypeptide together with a permeation-enhancing mixture to enhance bioavailability is described for example in U.S. Pat. No. 6,008,187.

Methods of formulating a peptide composition of the invention will be readily appreciated by persons of ordinary skill in the art to which the invention relates. Nonetheless, guidance may be found in Gennaro A R: Remington: The Science and Practice of Pharmacy, 20th ed., Lippincott, Williams & Wilkins, 2000.

As will be appreciated, the dose of a peptide (or composition comprising same) administered, the period of administration, and the general administration regime may differ between subjects depending on such variables as mentioned herein before. However, by way of general example, the inventors contemplate administration of from approximately 30 μg to 300 mg per kilogram (mg/Kg) mass of the animal, for example, 0.3 to 30 mg/Kg, with lower doses such as 0.003 to 0.3 mg/Kg, e.g. about 0.03 mg/Kg, being appropriate for administration through the cerebrospinal fluid (for example, which may be appropriate in treatment of encephalitis including multiple sclerosis) such as by intracerebroventricular administration, and higher doses such as 3 to 300 mg/Kg, e.g. about 30 mg/Kg, being appropriate for administration by methods such as oral, systemic (eg. transdermal), or parenteral (e.g. intravenous) administration.

Gene Therapy—Compositions and Modes of Administration

As mentioned herein before, methods of the invention may involve the administration of nucleic acids encoding peptides of the invention and/or constructs comprising same. The use of such nucleic acid techniques may be referred to herein as "gene therapy".

Any of the methods for gene therapy available in the art can be used according to the present invention. Exemplary methods are described below. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5):155-215).

Methods commonly known in the art of recombinant DNA technology which can be used in generating appropriate constructs or vectors are described generally herein before and more specifically for example in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one aspect, a composition comprising at least nucleic acid sequences encoding a peptide of the invention in expression vectors are administered to suitable hosts. The expression of nucleic acid sequences encoding a peptide of the invention may be optimized by enlarging the sequence either by including repeats of the peptide sequence or including flanking heterologous sequences to enable the sequence to be expressed, and processed by the translational machinery. The sequence may be fused with a signal peptide and cell-permeable peptide to allow for secretion, and cell uptake. The expression of nucleic acid sequences encoding a peptide of the invention may be regulated by any inducible, constitutive, or tissue-specific promoter known to those of skill in the art. In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. In a particular embodiment, nucleic acid molecules encoding a peptide of the invention are flanked by regions that promote homologous recombination at a desired site in the genome, thus providing for intrachromosomal expression of said coding regions (Koller and Smithies, 1989, Proc. Natl. Acad. Sci. USA 86:8932-8935; Zijlstra et al., 1989, Nature 342:435-438).

Delivery of the nucleic acids into a patient may be either direct, in which case the patient is directly exposed to the nucleic acid molecules or constructs containing them, or indirect, in which case, cells are first transformed with the nucleic acid molecules in vitro to express secretable cell-permeable forms of the peptide, and then transplanted into the patient. These two approaches are known, respectively, as in vivo or ex vivo gene therapy.

In a specific embodiment, the nucleic acid molecules are directly administered in vivo, where they are expressed to produce the encoded product. This can be accomplished by any of numerous methods known in the art; for example, they may be constructed as part of an appropriate nucleic acid expression vector and administered so that they become intracellular, e.g., by infection using defective or attenuated retroviral or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), and the like.

In another embodiment, nucleic acid-ligand complexes can be formed in which the ligand comprises a fusogenic viral peptide to disrupt endosomes, allowing the nucleic acid molecules to avoid lysosomal degradation.

In yet another embodiment, the nucleic acid molecules can be targeted in vivo for cell specific uptake and expression, by targeting a specific receptor (as described for example in WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.); and, WO 93/20221 dated Oct. 14, 1993 (Young)). Alternatively, the nucleic acid molecules can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

In a specific embodiment, viral vectors are used to express nucleic acid sequences. Persons of skill in the art to which the invention relates may appreciate a variety of suitable viral vectors having regard to the nature of the invention described herein. However, by way of example, a retroviral vector can be used (see Miller et al., 1993, Meth. Enzymol. 217:581-599). Such retroviral vectors have deleted retroviral sequences that are not necessary for packaging of the viral genome and integration into host cell DNA. More detail about retroviral vectors can be found in Boesen et al., 1994, Biotherapy 6:291-302, for example. Other references illustrating the use of retroviral vectors in gene therapy include, for example: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. In Genetics and Devel. 3:110-114.

Another example of a suitable viral vector of use in gene therapy techniques applicable to the invention includes adenoviruses. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783.

Adeno-associated virus (AAV) has also been proposed for use in gene therapy (Walsh et al., 1993, Proc. Soc. Exp. Biol. Med. 204:289-300; U.S. Pat. No. 5,436,146). AAV present the most preferable viral vectors for use in the present invention. AAV vectors have been reported to lead to persistent (>6 months) expression of a transgene in both gut epithelial cells and hepatocytes, resulting in long-term phenotypic recovery in a diabetic animal model (Xu, RA et al., 2001, Peroral transduction of diffuse cells and hepatocyte insulin leading to euglycemia in diabetic rats, Mol Ther 3:S180; During, M J et al., 1998, Peroral gene therapy of lactose intolerance using an adeno-associated virus vector, Nature Med. 4:1131-1135; During M J et al., 2000, An oral vaccine against NMDAR1 with efficacy in experimental stroke and epilepsy, Science 287:1453-1460). AAV is a nonpathogenic, helper-dependent member of the parvovirus family with several major advantages, such as stable integration, low immunogenicity, long-term expression, and the ability to infect both dividing and non-dividing cells. It is capable of directing long-term transgene expression in largely terminally differentiated tissues in vivo without causing toxicity to the host and without eliciting a cellular immune response to the transduced cells (Ponnazhagan S et al., 2001, Adeno-associated Virus for Cancer Gene Therapy, Cancer Res 61:6313-6321; Lai C C et al., 2001, Suppression of choroidal neovascularization by adeno-associated virus vector expressing angiostatin, Invest Ophthalmol Vis Sci 42(10):2401-7; Nguyen J T et al., 1998, Adeno-associated virus-mediated delivery of antiangiogenic factors as an antitumor strategy, Cancer Research 58:5673-7).

In a preferred embodiment of the invention, the cells into which a nucleic acid can be introduced for purposes of gene therapy are leukocytes. However, any desired, available cell type, could be used, especially where the nucleic acid is adapted to express a peptide to be secreted from the cell and subsequently taken up by a leukocyte. For example, the nucleic acid may be introduced into epithelial cells, endothelial cells, keratinocytes, fibroblasts, muscle cells, hepatocytes; blood cells such as T lymphocytes, B lymphocytes, monocytes, and macrophages.

As mentioned herein before, nucleic acids and nucleic acid constructs of use in this aspect of the invention may be formulated into appropriate compositions in association with one or more pharmaceutically acceptable diluents, carriers and/or excipients. Skilled persons will readily appreciate such suitable diluents, carriers and/or excipients. However, by way of specific example, suitable liquid carriers, especially for injectable solutions, include water, aqueous saline solution, aqueous dextrose solution, and the like, with isotonic solutions being preferred.

The nucleic acids, constructs and viruses may be formulated to help assist in delivery, or protect the integrity of the nucleic acid in vivo. For example, they may be formulated into liposomes, microparticles, microcapsules, or recombinant cells, or as a part of appropriate viral vectors. They may also be formulated to make use of delivery by receptor-mediated endocytosis (see, e.g., Wu and Wu, J. Biol. Chem. 262:4429-4432 (1987)). Lipid Polycation DNA (LPD) may be employed in which DNA is condensed prior to encapsulation in the lipid (as used by Targeted Genetics Corporation, Seattle, Wash., USA).

Specific examples of methods of administering a gene-therapy-based composition of the invention include, but are not limited to, parenteral administration (e.g., intradermal, intramuscular, intraperitoneal, intravenous and subcutaneous), epidural, and mucosal (e.g., intranasal and oral routes). In a specific embodiment, prophylactic or therapeutic compositions of the invention are administered intramuscularly, intravenously, or subcutaneously. The composition may be administered by any convenient route, for example by infusion or injection, by absorption through epithelial or mucocutaneous linings (e.g., oral mucosa, rectal and intestinal mucosa, etc.) and may be administered together with other biologically active agents. Administration can be systemic or local. Systemic gene-therapy via intravenous administration provides a preferable mode of administration.

Methods of Identification of Functional Interactor Molecules and Mimetics

Methods of identifying β7 integrin functional interactor molecules, including interference molecules (such as aptamers), and mimetics of the peptides of the invention, will generally comprise at least the step of bringing a potential functional interactor or interference molecule in contact with a peptide of the invention and observing whether or not binding occurs. For example, such molecules can be identified by "pull-down" assays whereby a peptide of the invention is immobilised on a matrix e.g., Sepharose beads and used to affinity isolate interactors from a cell lysate. The interactors can be electrophoresed on an SDS-gel and identified by Western blotting with mAbs against candidate interactors, or the interactors are identified directly by mass spectroscopy. The peptides of the invention may be immobilised on a column, and used to affinity purify interactors. BiaCORE technology based on surface plasmon resonance can be used to establish or characterise molecular interactions.

It should be appreciated that the peptides may also be used to screen libraries of molecules for potential interactors; for example aptamer libraries (such as those of Archemix, Cambridge, Mass.), libraries of chemical mimetics (as may be known in the art) and libraries of synthetic antibodies (for example, HuCAL® antibody libraries (Morphosys AG, Martinsried/Planegg, Germany)).

Once binding to a peptide of the invention has been established, the function of a candidate molecule, can be assessed, for example, using in vitro cell adhesion assays as described in the "Examples" section herein after. Interactors can also be over-expressed or inhibited (e.g., with antisense, RNAi etc) to determine whether they regulate the function of β7 integrins. Skilled persons may readily appreciate alternative assays, including in vivo assays in animals.

"Interference molecules" will exhibit at least some ability to disrupt or inhibit the activity and function of a β7 integrin. Preferably they will disrupt or prevent the interaction of β7 integrins with their ligands.

Antibodies

Peptides of the invention may be used as antigens for the production of antibodies. Such antibodies may have specific application in experimental studies of the functions of β7 integrins, or as prophylactic or therapeutic reagents when rendered cell-permeable. Anti-idiotypic antibodies raised against antibodies that recognise peptides of the invention may be used to identify potential interactors, or for therapy.

The term "antibody" should be understood in the broadest possible sense and is intended to encompass, for example, intact monoclonal antibodies, polyclonal antibodies, and derivatives of such antibodies; for example, hybrid and recombinant antibodies (for example, humanised antibodies, diabodies, triabodies, and single chain antibodies) and antibody fragments so long as they exhibit the desired biological activity. An antibody may also be modified so as to render it cell-permeable (a "Transbody"). This may be achieved using the membrane translocation motif technology described herein before. In addition, the methodology described by Heng and Cao (Med Hypotheses. 2005; 64(6):1105-8) may be used.

Antibody "fragments" is intended to encompass a portion of an intact antibody, generally the antigen binding or variable region of the antibody. Examples of antibody fragments include Fab, Fab' F(ab')$_2$, and Fv fragments. Those of ordinary skill in the art to which the invention relates will recognise methods to generate such antibody fragments. However, by way of general example proteolytic digestions of intact antibodies may be used, or the fragments may be directly produced via recombinant nucleic acid technology.

"Humanised" antibodies are essentially hybrid or chimeric antibodies containing domains derived from human sources and domains derived from the animal in which an antibody may have been generated. In the present case, they are either fully-human or mouse/human-hybrid antibodies. Humanised antibodies in accordance with the invention will generally comprise the mouse CDR (complementarity determining region or antigen binding site) of an antibody against of peptide of the invention fused to appropriate human antibody domains or regions necessary to form a functional antibody, for example. Humanization of murine antibodies can be achieved using techniques known in the art, for example by epitope-guided selection (Wang et al, 2000). The methods of Jones et al (1986), or Maynard and Georgiou (2000) provide further examples.

Humanisation of antibodies may help reduce the immunogenicity of the antibodies of the invention in humans for example. Reduced immunogenicity can be obtained by transplanting murine CDR regions to a homologous human β sheet framework (termed CDR grafting; refer to Riechmann et al 1988 and Jones et al 1986).

Those of skill in the art to which the invention relates will appreciate the terms "diabodies" and "triabodies". These are molecules which comprise a heavy chain variable domain (VH) connected to a light chain variable domain (VL) by a short peptide linker that is too short to allow pairing between the two domains on the same chain. This promotes pairing with the complementary domains of one or more other chain encouraging the formation of dimeric or trimeric molecules with two or more functional antigen binding sites. The resulting antibody molecules may be monospecific or multispecific (e.g., bispecific in the case of diabodies). Such antibody molecules may be created from two or more of the antibodies of the present invention using methodology standard in the art to which the invention relates; for example, as described by Holliger et al (1993), and Tomlinson and Holliger (2000).

The production of antibodies in accordance with the invention may be carried out according to standard methodology in the art. For example, in the case of the production of polyclonal antibodies the method of Diamond et al (1981) may be used. Monoclonal antibodies may be prepared, for example, as described in Current Protocols in Immunology (1994, published by John Wiley & Sons and edited by: John E. Coligan, Ada M. Kruisbeek, David H. Margulies, Ethan M. Shevach, Warren Strober), by Winter and Milstein (1991), or in "Monoclonal Antibody Production Techniques and Applications", Marcel Dekker Inc.

Production of an antibody or derivative thereof may also be achieved using standard recombinant techniques known in the art, and discussed previously herein. It will be appreciated that nucleic acids encoding an antibody, and thus suitable for recombinant production of the antibody, may be identified by isolating and sequencing nucleic acids from an appropriate hybridoma, or by having regard to the amino acid sequence of the antibody and knowledge of the genetic code and degeneracy therein. The amino acid sequence of an antibody of the invention may be determined using standard methodology; for example, the technique of Edman degradation and HPLC or mass spectroscopy analysis (Hunkapiller et al, 1983), may be used.

The inventors consider recombinant techniques to be a preferable means of producing antibodies on a commercial scale for therapeutic applications.

Antibodies or derivatives thereof may be formulated into pharmaceutical compositions in a similar manner as described herein before, particularly in relation to formulation of the peptides of the invention (see in particular the sections entitled "compositions and methods of treatment" and "peptide compositions and modes of administration"). Antibodies may also be administered in accordance with the principles described in those sections. Improved delivery methods for antibodies include controlled-release and local delivery strategies as described, for example, by Grainger (in "Controlled-release and local delivery of therapeutic antibodies", Expert Opin Biol Ther. 2004 July; 4(7):1029-44).

Antibodies may also be delivered to a subject in the form of "intrabodies", or nucleic acid constructs which are adapted to express the antibodies in desired cells following plasmid or viral delivery, for example. Inasmuch as this is the case, appropriate nucleic acids can be formulated into acceptable pharmaceutical compositions and administered as herein before described in the sections entitled "compositions and methods of treatment" and "gene-therapy—compositions and modes of administration. Stocks (in Intrabodies: production and promise. Drug Discov Today. 2004 Nov. 15; 9(22): 960-6.) provides further guidance on the production of "intrabodies".

Kits

The peptides and nucleic acids of the invention may be used in kits suitable for modulating the function of integrin β7 or for the treatment of integrin β7-mediated inflammatory disorders. Such kits will comprise at least a peptide or nucleic acid of the invention in a suitable container. The nucleic acid or peptide may be formulated in a pharmaceutical composition ready for direct administration to a subject. Alternatively, the kit may comprise the peptide or nucleic acid in one container and a pharmaceutical carrier composition in another; the contents of each container being mixed together prior to administration. The kit may also comprise additional agents and compositions in further separate containers as may be necessary for a particular application. Further, kits of the invention can also comprise instructions for the use and administration of the components of the kit.

Any container suitable for storing and/or administering a pharmaceutical composition may be used in a kit of the invention. Suitable containers will be appreciated by persons skilled in the art. By way of example, such containers include vials and syringes. The containers may be suitably sterilised and hermetically sealed.

EXAMPLES

Materials and Methods

Cell Lines and synthetic peptides. The mouse spontaneous AKR/Cum Y CD8 LPAM-1$^+$/VLA4$^-$ T lymphoma cell line TK-1, and the human T lymphoma cell line H9, were purchased from the American Type Culture Collection, Rockville, Md. They were cultured at 37° C. in RPMI 1640 medium supplemented with 50 U/ml penicillin, 50 µg/ml streptomycin, 200 µg/ml L-glutamine, 10% (v/v) FCS and 0.05 mM β-mercaptoethanol. All synthetic peptides were custom made by Mimotopes Pty Ltd., Victoria, Australia. The β7 cytoplasmic domain peptides were N-terminally fused during synthesis to biotinylated penetratin (RQIKIWFQNR-RMKWKKFDRREF (SEQ ID NO. 18)) or to a biotinylated R9 polymer (SEQ ID NO. 19) to render them cell-permeable.

GST-fusion protein encoding the integrin β7 subunit cytoplasmic domain. A pGEX-2T vector encoding the complete β7 cytoplasmic domain was kindly provided by Dr Andrew Lazarovits (Imperial Cancer Research Fund, London).

Recombinant MAdCAM-1-Fc, VCAM-1-Fc, and ICAM-1-Fc chimeras. The production of soluble recombinant mouse MAdCAM-1-Fc from insect cells using a baculovirus expression system has been described previously (24). The soluble human VCAM-1-Fc and ICAM-1-Fc chimeras were produced using the glutamine synthetase gene amplification system. The extracellular portions of human VCAM-1 and ICAM-1 fused to the Fc domain of human IgG1 were expressed from the pEE14 vector (kindly provided by Dr. Chris Bebbington, Celltech Ltd., UK) in CHO K1 cells as described previously (25). MAdCAM-1-Fc-coated microspheres were prepared by mixing 1 µg of recombinant MAd-CAM-1-Fc with 1 µl of a 1% suspension of Power-bind protein A microparticles (Seradyn, 0.979 mM diameter) in 100 µl for 30 min at 4° C.

Peptide internalization and visualization. Biotinylated peptides at 20 µM were added to the cells in serum-free RPMI 1640 medium for 30 min at 37° C., or 60 min at room temperature. After washing with PBS, cells were resuspended into PBS/1% FCS and cytocentrifuged onto glass slides. Cytospin smears were fixed with 4% paraformaldehyde in PBS for 15 min at room temperature, washed twice with PBS and permeabilized in PBS containing 0.2% Triton X-100 for 10 min. Biotinylated peptide was detected by incubating the slides with streptavidin-FITC (Sigma, Mo.), and visualized using a Leica TCS 4D confocal laser microscope. Images were processed using Leica Scanware™ 4.2 A software and Adobe Photoshop 5.0.

Cell adhesion assays. Lab-Tek 16-well glass slides (Nunc) or flat-bottomed 96-well maxisorb plates (Nunc) were coated with purified mouse MAdCAM-1-Fc, human VCAM-1-Fc, and human ICAM-1-Fc (70 to 100 µl of 5 to 10 µg/ml), and incubated at 4° C. overnight. Slides were washed once with PBS, and blocked with FCS for 2 h at room temperature. Slides were washed with Hanks balanced salt solution (HBSS) containing 10 mM Hepes. Cells were either left unlabeled or labeled with the fluorescent dye chloromethyl fluorescein diacetate (CMFDA; Molecular Probes, Oregon), and activated by resuspension in HBSS containing 10 mM Hepes supplemented with 2 mM $Ca^{++}$ and 2 mM $Mn^{++}$. Cells were alternatively activated with 50 ng/ml PMA, or by incubating with $AlF4^-$ (10 mM NaF and 40 M AlCl3). They were preincubated with peptides at different concentrations for 10 min at room temperature, checked for viability by trypan blue exclusion, and then $10^6$ cells added to each coated well and left to adhere for 30 min at room temperature. Non-adherent unlabeled cells in 16-well glass slides were removed by twice dipping slides gently into PBS, and adherent cells fixed in PBS containing 2% (v/v) glutaraldehyde for at least 3 h. The number of adherent cells was determined by counting the number of adherent cells in four independent fields at 100× magnification under an inverted microscope. Alternatively, non-adherent CMFDA-labeled cells in 96-well plates were removed by inverse centrifugation at 70×g for 5 min into 50 mM Tris pH 7.5, 150 mM NaCl, 2 mM $MnCl_2$, followed by gentle washing with a pipette. The fluorescence of CMFDA-labeled adherent cells was measured using a VICTOR 1420 multilabel counter (Wallac). Unless otherwise stated, experiments were repeated in triplicate, using duplicate wells.

Confocal microscopy analysis of receptor clustering. TK-1 cells were incubated in the presence or absence of peptides (50 µM) for 1 h at room temperature, and cells were activated for 30 min at room temperature in HBSS containing 2 mM Ca++ and $AlF4^-$. Cells were incubated with MAdCAM-1-coated microspheres for 1 h on ice. They were washed with PBS containing 0.02% sodium azide, and fixed in 4% (w/v) paraformaldehyde in PBS for an additional 1 h. They were then stained with FITC-conjugated anti-β7 subunit M293 mAb, washed and fixed as above. Cells were mixed 1:1 with Citifluor glycerol/PBS solution, mounted on slides, and analyzed using a Leica TCS4D confocal laser scanning microscope equipped with an external argon-krypton laser (488 nm). Images were digitally recorded and printed on an Epson colour printer using Microsoft Power Point software.

Phosphorylation of recombinant GST fusion protein encoding β7cyt. H9 cells ($5 \times 10^7$) were lysed at 4° C. in 1 ml of lysis buffer (10 mM Tris pH 7.4, 50 mM NaCl, 50 mM NaF, 1 mM sodium orthovanadate, 300 µg/ml PMSF, 20 µg/ml aprotinin, 10 µg/ml leupeptin, and 1% NP-40), centrifuged, and the supernatant precleared with GST-Sepharose. A GST fusion protein (50 µg) encoding the β7 subunit cytoplasmic domain bound to glutathione-Sepharose was incubated with trace amounts (1:100 dilution) of precleared lysate for 2 h at 4° C. The beads were washed thrice with lysis buffer and thrice with kinase buffer (10 mM Tris pH 7.4, 50 mM NaCl, 5 mM $MgCl_2$, 5 mM $MnCl_2$, 0.1 mM $Na_3VO_4$), and incubated in 30 µl kinase buffer containing 0.5 µCi $[^{32}P]$ γATP for 20 min at 30° C. The sample was subjected to SDS-PAGE on a 10% acrylamide gel. The gel was stained with Coomassie Blue to visualize the GST fusion protein, and treated with 1 M KOH at 55° C. for 2 h to remove alkali-labile phosphate moieties on serine and threonine. The gel was dried, and subjected to autoradiography.

To confirm that the β7cyt was phosphorylated, GST-β7cyt beads subjected to an in vitro kinase assay were washed, and boiled in 10 µl of 10% SDS for 5 min. The supernatant was diluted to 1 ml, and precleared with 10% Streptococcal protein-G and rabbit Ig-Sepharose. The sample was divided, and one half immunoprecipitated with 50 µl of rabbit polyclonal antisera against β7cyt, and the other half with 50 µl of normal rabbit sera. The immunoprecipitates were resolved by SDS-PAGE, and autoradiographed.

Assay to test whether β7 cytoplasmic domain peptides bind a kinase(s). TK-1 cells ($3 \times 10^6$) were lysed in 1 ml of lysis buffer, and centrifuged at 12,000×g for 10 min at 4° C. Supernatants were precleared with 10 µl of Sepharose and then 10 µl of streptavidin-Sepharose. Cytoplasmic domain peptides were screened for their ability to associate with a kinase in lysates of TK-1 cells that were either left unactivated or had been activated with $AlF4^-$. Biotinylated peptides immobilized on 5 µl of streptavidin-Sepharose were incubated with 1 ml of lysis buffer containing 1 µl of cell lysate for 2 h at 4° C. with gentle shaking. The beads were washed thrice with ice-cold lysis buffer, once with kinase buffer, and were incubated with 30 µl kinase buffer and 0.5 to 1 µCi γ-ATP for 20 min at 30° C. Beads were washed five times, and radioactivity measured in a scintillation counter.

Results

Figures 2A, 2B, 2C, 2D, 2E, 2F, 2G:
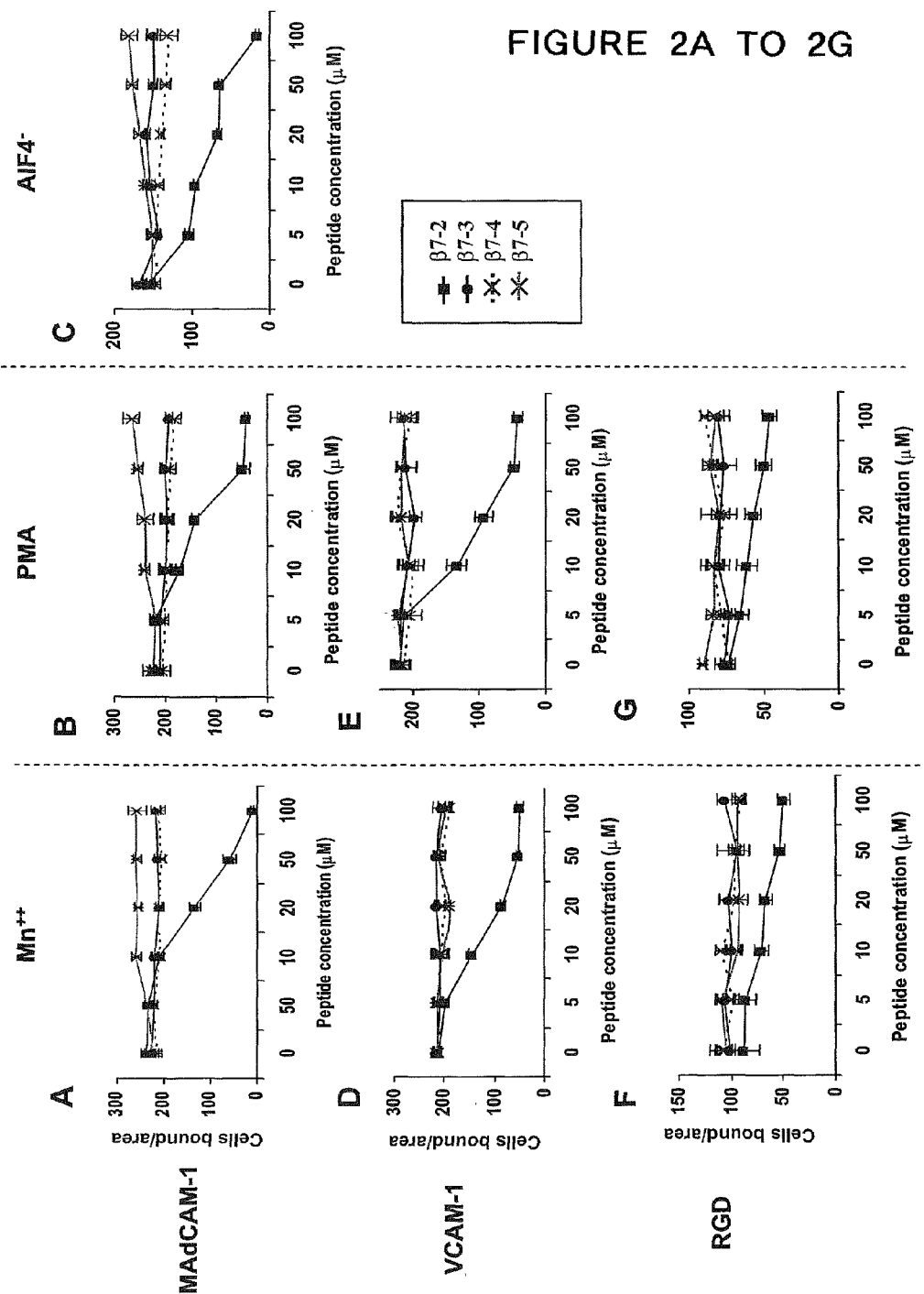

A cell-permeable peptide containing a membrane-proximal region of the β7 cytoplasmic domain inhibits α4β7-mediated T cell adhesion. Seven overlapping peptides (β7-2 to β7-9) encompassing the entire 52 amino acid residue cytoplasmic domain of the β7 subunit (β7cyt) (FIG. 1A) were fused at their N-termini to penetratin, a 16 amino acid residue fragment of the third helix of the homeodomain of Antennapedia (26, 27). The peptides (50 µM) were incubated with TK-1 T cells ($\alpha4^+$ $\beta7^+$ $\beta1^-$) to determine whether they had been rendered cell-permeable by penetratin. All seven peptides were imported into the cytoplasm of cells after 1 h, but were excluded from the nucleus (FIG. 1B). When peptides β7-2 to β7-5, which together spanned the entire cytoplasmic domain, were tested for their abilities to block "inside-out" signalling (FIG. 2A-G), only the β7-2 peptide encompassing residues 729-740 abrogated TK-1 cell adhesion to the immobilised α4β7 ligands MAdCAM-1 (FIG. 2A-C), VCAM-1 (FIG. 2D, E), and an engineered polymer of RGD (FIG. 2F, G). Cell-binding to MAdCAM-1 and VCAM-1 was almost completely blocked at 100 µm of peptide, whereas there was only a 50% reduction in binding to the RGD polymer (FIG. 2F, G). Similar levels of inhibition were achieved irrespective of whether the cell activator was the pan-activator $Mn^{++}$ (FIG. 2A, D, F), the protein kinase C (PKC) activator PMA (FIG. 2B, E, G), or the G-protein activator $AlF4^-$ in the case of MAdCAM-1 (FIG. 2C).

A cell adhesion regulatory domain (CARD) from the extreme C-terminus (residues 747 to 762) of the integrin β3 subunit has been reported to inhibit the adhesion of erythroleukaemia and endothelial cells to immobilized fibrinogen (28). As expected, a cell-permeable control peptide (β3-CARD) containing the β3 CARD fused N-terminally to penetratin (FIG. 1A, B) had no effect on β7-mediated adhesion of $Mn^{++}$, $AlF4^-$, or PMA-activated TK-1 cells to MAdCAM-1, and VCAM-1 (FIGS. 3A, B). The peptide did not block β3 integrin-mediated cell-binding to the RGD polymer (FIG. 3C), as TK-1 cells do not express β3 integrins (data not shown). Rather binding of TK-1 cells to RGD polymers is mediated by β7 integrins, as reported previously (29).

Similar experiments to those described above were carried out using the human T lymphoma cell line H9 ($\alpha4^+$ $\beta7^+$ $\beta1^+$) to demonstrate that peptide β7-2-mediated blockade of lymphocyte adhesion was not species-specific. Peptides were imported into this cell line at a rate similar to that observed with the TK-1 cell line (data not shown). Peptide β7-2 blocked $Mn^{++}$ (FIG. 4A, C), and PMA-activated (FIG. 4B, D) adhesion of H9 cells to MAdCAM-1 (FIG. 4A, B), and VCAM-1 (FIG. 4C, D), respectively, whereas peptides β7-3, β7-4, and β7-5 were completely ineffective. β7-2 peptide-mediated inhibition of H9 cell adhesion to VCAM-1 was not quite as effective as blockade of TK-1 cell adhesion, as evidenced by the higher concentrations of peptide required to block cell adhesion, presumably because H9 cells express α4β1 which preferentially mediates cell binding to VCAM-1. In contrast, the β3 CARD peptide failed to block the adhesion of Mn$^{++}$ and PMA-activated H9 cells to MAdCAM-1 and VCAM-1 (data not shown).

Inhibition of Cell Adhesion by Peptide β7-2 is β7 Integrin-Specific.

Figures 4A, 4B, 4C, 4D, 4E:
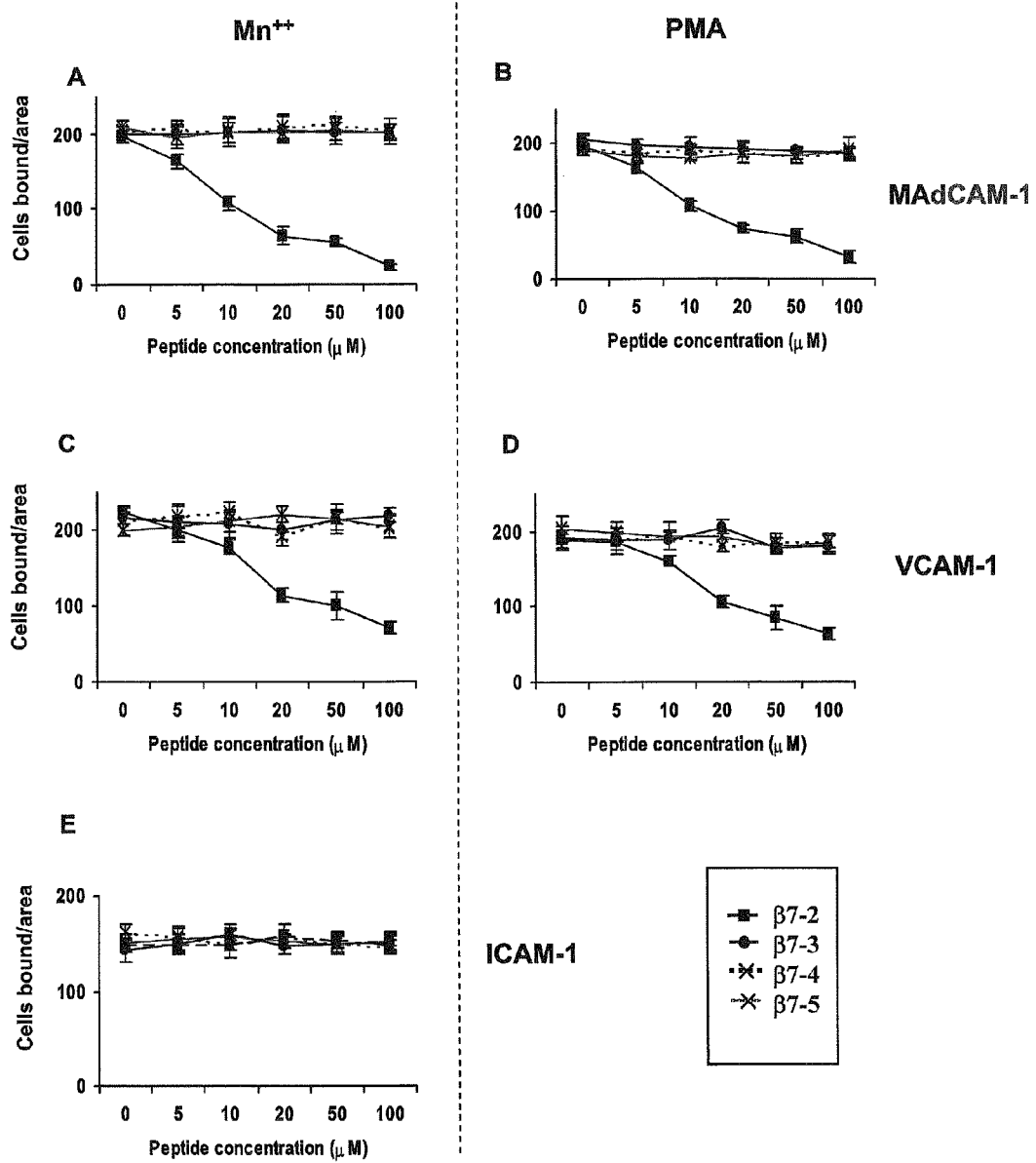

H9 cells express the β2 integrin αLβ2, and bind to the αLβ2 ligand ICAM-1 (FIG. 4E). None of the β7 cytoplasmic domain peptides (β7-2 to β7-5) inhibited Mn$^{++}$-activated H9 cells from binding to ICAM-1, demonstrating that the inhibitory activity of the β7-2 peptide is restricted to β7 integrins (FIG. 4E).

Figure 5A:
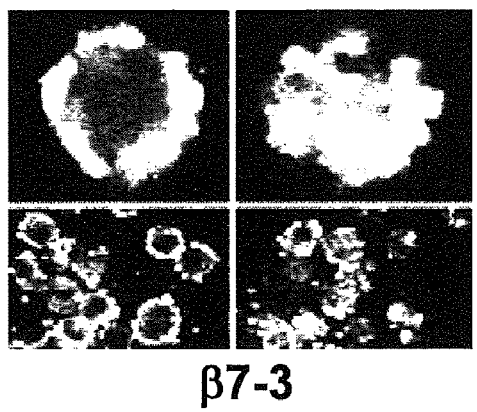
Figure 5A:
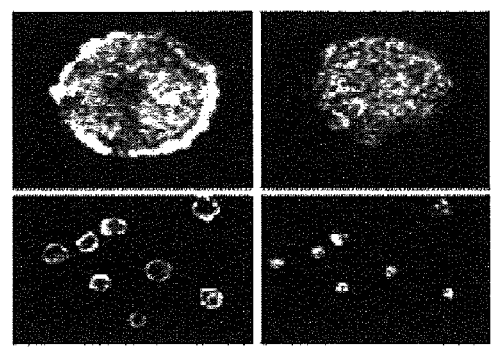
Figure 5A:
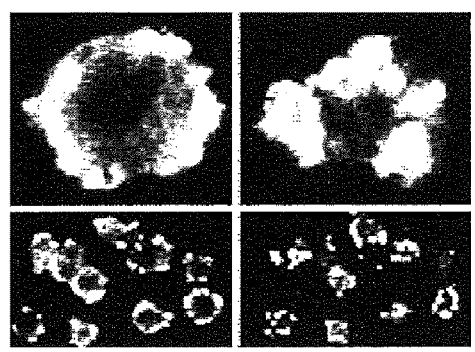
Figures 5B, 5C, 5D, 5E:
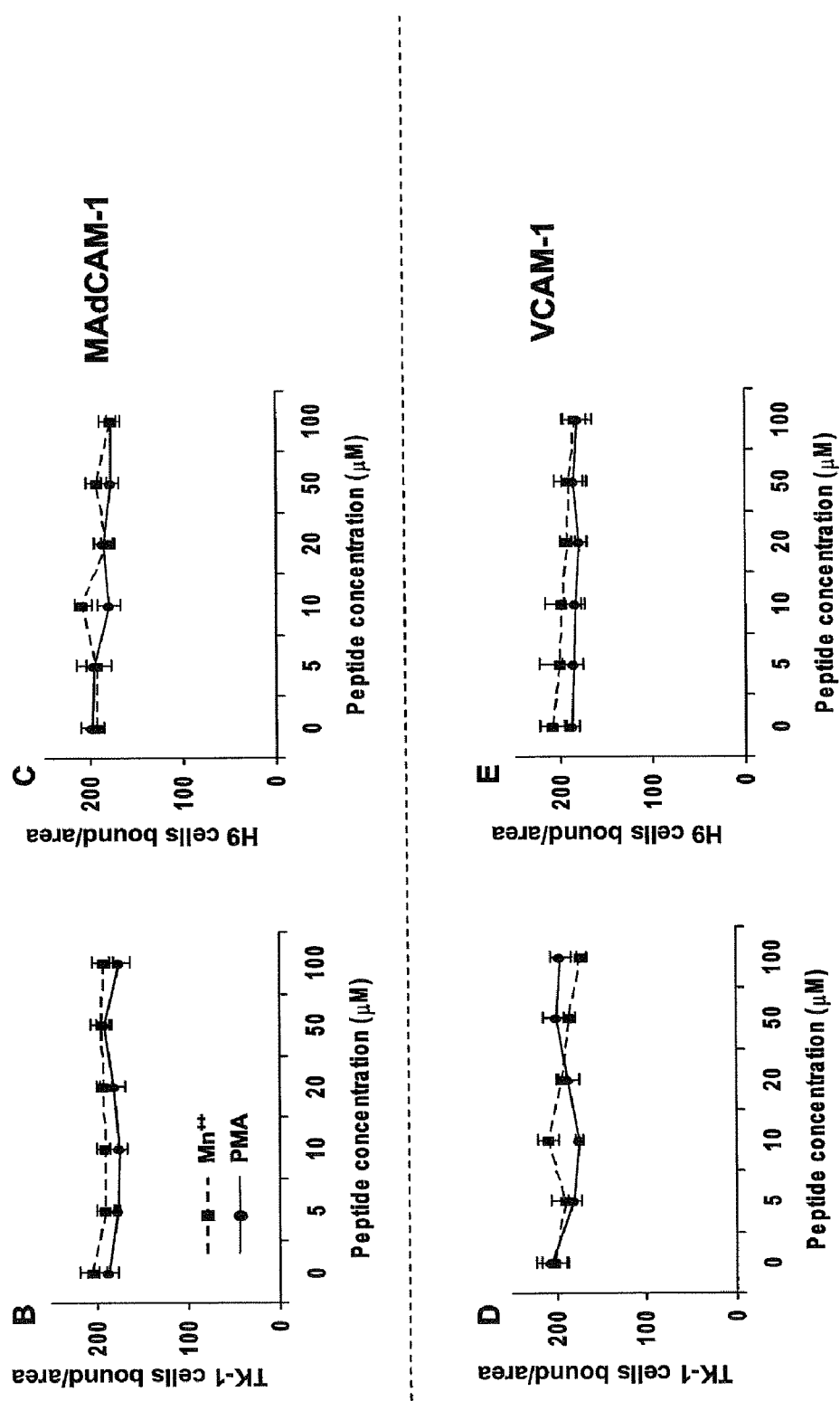

Cell-permeable peptide β7-2 blocks ligand-induced clustering of α4β7, but is unable to disrupt established focal adhesions. Stimulation of TK-1 cells in the presence of MAdCAM-1 leads to ligand-induced clustering of α4β7 at the cell-surface, a process which appears largely responsible for increased α4β7-mediated cell adhesion (8). Peptide β7-2 completely blocked the MAdCAM-1-induced redistribution of α4β7 on the surface of AlF4$^-$-activated TK-1 cells, suggesting that the peptide prevents the formation of focal adhesion complexes (FIG. 5A). In contrast, the non-active peptide β7-3 was without effect. The β7-2 peptide was not able to detach Mn$^{++}$ and PMA-activated TK-1 (FIG. 5B, D), and H9 (FIG. 5C, E) cells already adhered to MAdCAM-1 (FIG. 5B, C) and VCAM-1 (FIG. 5D, E), suggesting it could not disrupt established focal adhesions.

A six amino acid residue motif is essential for cell adhesion. The β7-2 peptide was divided into two to give the cell-permeable peptides β7-7, and β7-8 (FIG. 1A, B), in order to sublocalize the region responsible for peptide blockade of cell adhesion. Peptide β7-8 encompassing residues 735-740 retained the ability to block Mn$^{++}$, PMA, and AlF4$^-$-activated TK-1 cell adhesion to MAdCAM-1, VCAM-1, and RGD polymer (FIG. 6), with a similar dose-dependency to that exhibited by peptide β7-2 (FIG. 2). In contrast, peptide β7-7 (residues 729-735) was completely ineffective. The β7-8 peptide also blocked the adhesion of H9 cells to the latter ligands (data not shown).

Figures 7A, 7B, 7C, 7D, 7E:
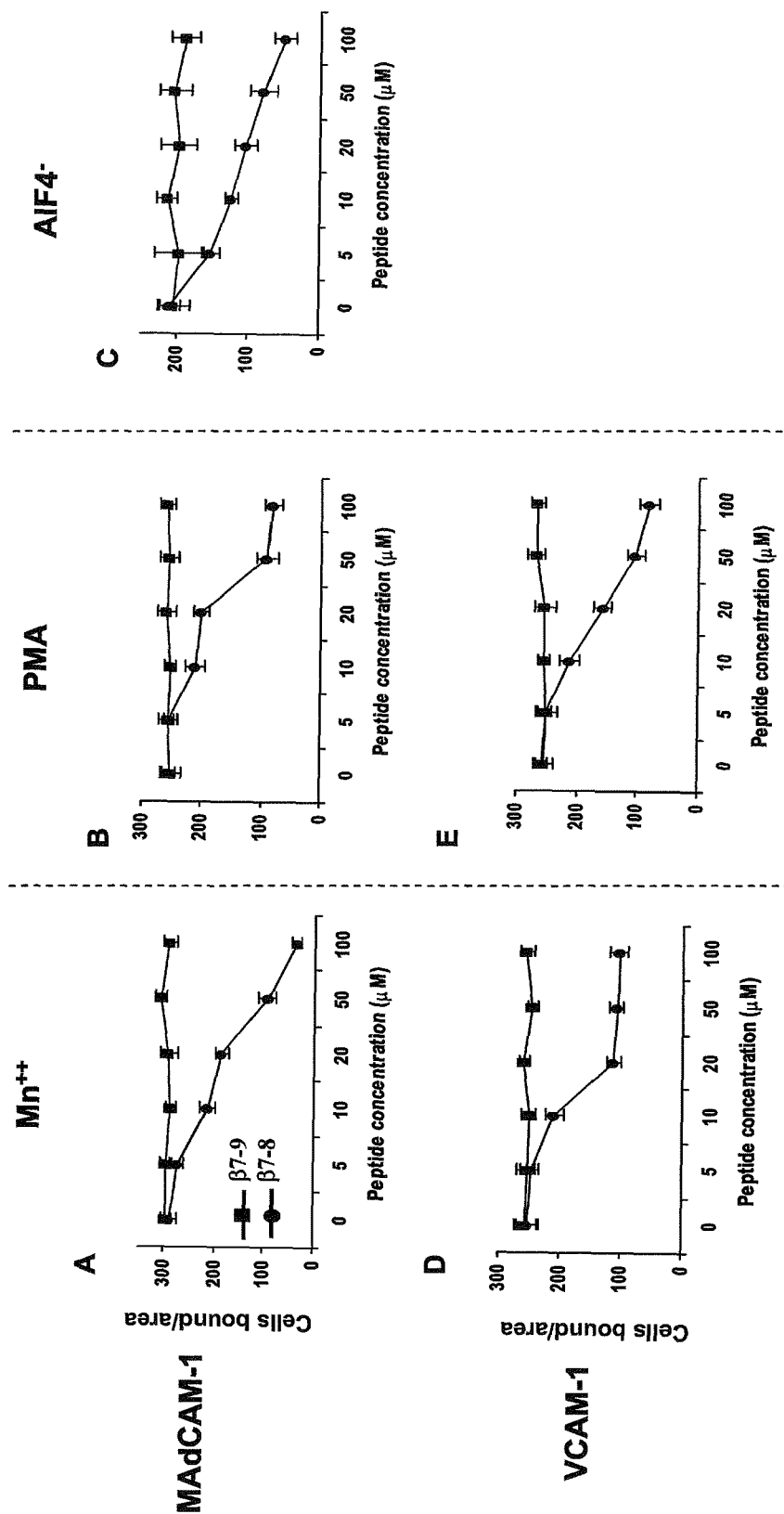

Tandem tyrosine residues in the β7 CARD are critical for the inhibitory activity of peptide β7-8. A mutant peptide (β7-9) in which both tyrosine residues 735 and 740 of YDRREY (SEQ ID NO. 1) had been substituted for phenylalanines was not able to inhibit the adhesion of Mn$^{++}$, PMA, and AlF4$^-$-activated TK-1 (FIG. 7) and H9 cells (data not shown) to either MAdCAM-1 (FIG. 7A-C), or VCAM-1 (FIG. 7D,E).

Recently, it was discovered that polymers of L-arginine (R) of 6 amino acids in length or greater are highly cell-permeable (30). Peptide β7-12 containing the YDRREY (SEQ ID NO. 1) peptide fused to a D-isomeric form of a nine arginine polymer was rapidly internalized by cells (FIG. 8A), and inhibited the adhesion of Mn$^{++}$, PMA, and AlF4$^-$-activated TK-1 cells to MAdCAM-1 (FIG. 8B), indicating that the cell adhesion blocking effect of the β7 CARD was independent of the type of carrier peptide. Truncation of peptide β7-12 to individually remove the flanking tyrosine residues 735 (peptide β7-10) and 740 (peptide β7-11) destroyed the activity of the peptide, as peptides β7-10 and β7-11 were not able to inhibit the adhesion of Mn$^{++}$, PMA, and AlF4$^-$-activated TK-1 cells to MAdCAM-1 (FIG. 8B). Thus, both flanking tyrosine residues are critical for activity, and YDRREY (SEQ ID NO. 1) defines the minimal motif.

A D-amino acid form of the β7 CARD retains activity. A D-amino acid version of the β7 CARD fused to a D-isomeric form of R9 was internalized by TK-1 cells (FIG. 8A), and was as equally potent as the L-enantiomer at inhibiting the adhesion of TK-1 T cells to immobilized VCAM-1-Fc (FIG. 8C). The D-amino acid form was cytotoxic at concentrations exceeding 50 μM, causing 50% cell death at 100 μM (data not shown).

Figure 9D:
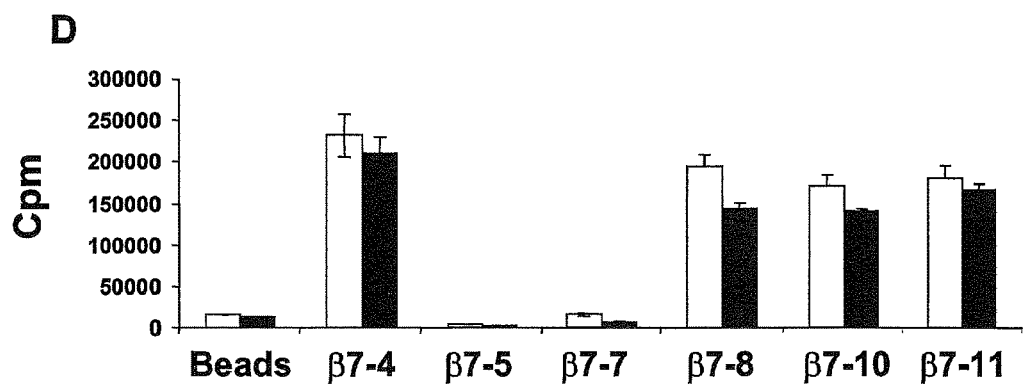

The β7 CARD binds a kinase(s), and tyrosine residues in the β7 CARD are phosphorylatable. Peptide β7-8 possesses two of the three potential β7cyt tyrosine phosphorylation sites (residues 735, 740, and 760) in β7cyt. An in vitro kinase assay revealed that β7cyt can be phosphorylated on tyrosine by a kinase(s) present in lymphocyte lysates (FIG. 9A). The prominent phosphorylated band formed with the GST-β7cyt fusion protein in FIG. 9A (lane β7) was specifically immunoprecipitated by a rabbit anti-β7cyt antibody (FIG. 9B). Inclusion of genistein at 20 μM completely blocked the phosphorylation of β7cyt, indicating that the phosphorylation was tyrosine-specific (FIG. 9C). The β7-4, β7-5, β7-7, β7-8, β7-10, and β7-11 peptides were each tested for their ability to associate with a kinase(s) and/or be phosphorylated. Peptides immobilized on Sepharose beads were incubated with lysates from unactivated and AlF4$^-$-activated cells, the beads washed, and subjected to an in vitro kinase assay to detect the presence of an associated kinase(s). Peptides β7-8, β7-10, and β7-11 formed a phosphorylated complex following treatment with a TK-1 cell lysate, as did peptide β7-4 containing tyrosine 760 within the NPLY motif (FIG. 9D). Thus, kinases interact with both the YDRREY (SEQ ID NO. 1) and QLNWKQDSNPLYKSAITTT (SEQ ID NO. 22) sequences within the N- and C-terminal regions of the cytoplasmic domain of the β7 subunit. Phosphorylated complexes were formed irrespective of whether lysates of unactivated or AlF4$^-$-activated cells were used, suggesting either that activation was not required, or the kinase(s) were activated after disruption of the cells. In contrast, peptide β7-7 and the extreme C-terminal control peptide β7-5 lacking potential tyrosine phosphorylation sites did not form a phosphorylated complex.

Discussion

The results herein reveal that the 6-amino acid peptide motif 735-YDRREY-740 (SEQ ID NO. 1) in the membrane proximal region of the cytoplasmic tail of β7 plays a critical role in mediating the clustering and adhesive function of β7 integrins. This motif is unique to the β7 cytoplasmic domain (FIG. 10), with the β1 and β5 subunits sharing the DRRE (SEQ ID NO. 37) core, but lacking the two flanking tyrosine residues. The YDRREY (SEQ ID NO. 1) motif has a certain symmetry, in that a core of two basic arginines, flanked by acidic residues, are contained by the tandem tyrosine residues. The β7 CARD is completely conserved between human and mouse β7cyt (FIG. 10). The β2 subunit is the only typical integrin β subunit that lacks the dibasic core, having a DLRE (SEQ ID NO. 38) motif instead. The DLRE (SEQ ID NO. 38) motif has been proposed to bind the GFFKR (SEQ ID NO. 39) motif common to all integrin α subunits, and to constrain LFA-1 into a low affinity state (31). Interestingly, substitution of a single amino acid to create the DRRE (SEQ ID NO. 37) motif within the β2 subunit induced clustering of LFA-1 at the cell-surface, and restored the PMA responsiveness of LFA-1 in K562 cells (32), suggesting that this motif controls receptor avidity via clustering as implied from the results of the present study.

Tyrosine residues 735 and 740 were both phosphorylatable and acted in tandem to mediate the adhesive function of α4β7.

Data looked at by the inventors indicates the CARD in β7 is unique to β7 integrins, suggesting that the adhesive function of β7 integrins may be regulated by a different intracellular signalling pathway compared to the likes of β1, β3 and β6 integrins. In accord, neither the cell permeable YDDREY (SEQ ID NO. 1) peptide nor the β3 CARD were able to block β2 integrin-mediated adhesion of H9 cells to ICAM-1 in the present study, indicating that the adhesivity of each of the β2, β3 and β7 integrins is differentially regulated.

Whilst not wishing to be bound by any particular theory the inventors believe that cell-permeable soluble forms of β7cyt compete for intracellular proteins that are critical for the cell-surface clustering of α4β7, and thereby abrogate α4β7-mediated cell adhesion. Whilst a large array of at least 21 proteins are known to bind one or more integrin β tails (43), so far only the actin-binding protein filamin (44), and the WD repeat protein WAIT-1 (25) have been reported in the published literature as binding to the β7 subunit. WAIT-1 specifically interacts with the cytoplasmic tail of the β7 subunit, but not the β1, and β2 subunits (25). The WAIT-1 binding site 729-RLSVEIYDR-740 (SEQ ID NO. 36) in β7cyt only partially overlaps the CARD in β7cyt. The filamin binding site in β7cyt has yet to be defined. Filamin-binding regions in the β1 and β2 integrin subunit cytoplasmic domains appears to differ. Thus, the filamin binding site in the β2 subunit was localized to the membrane proximal region (residues 724 to 747) (45), whereas all but three C-terminal residues were required in the case of the β1 subunit (46). Filamin is recruited to focal adhesions, provides a mechanical link between integrins and the cytoskeleton, and acts as an adapter protein for signaling molecules that regulate cytoskeletal dynamics (43). If the CARD in β7cyt binds filamin, this might explain, in part, the ability of the cell-permeable YDRREY (SEQ ID NO. 1) peptide to inhibit α4β7 cell-surface clustering.

Whilst the inventors have demonstrated that an extreme C-terminal β7cyt peptide failed to exhibit a dominant-negative affect on α4β7-mediated adhesion, it is clear that this region also plays a role in regulating β7 integrin function. Thus, deletion of a 34-amino acid residue segment from the C-terminus of β7cyt abrogated adhesion of 38C13 B lymphoma cells to β7 integrin ligands (47). It is possible that different regions of β7cyt assume cell-type specific functions.

In summary, a CARD in the cytoplasmic tail of the integrin β7 subunit has been identified that contributes to cell-surface clustering of α4β7, and thereby plays a critical role in mediating the adhesion of activated T cells. The CARD YDRREY (SEQ ID NO. 1) motif represents a molecule of use to modulate the adhesive functions of β7 integrins "from within" to treat several major inflammatory diseases to which β7 integrins contribute, and also provides a template to design further pharmaceutical drugs.

The invention has been described herein, with reference to certain preferred embodiments, in order to enable the reader to practice the invention without undue experimentation. However, a person having ordinary skill in the art to which the invention relates will readily recognise that many of the components and parameters may be varied or modified to a certain extent without departing from the scope of the invention. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment or any form of suggestion that that prior art forms part of the common general knowledge in the field of endeavour to which the invention relates.

Throughout this specification, and any claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

REFERENCES

1. Krissansen, G. W. Integrin superfamily. The Encyclopedia of Life Sciences. MacMillan Press, 2000.
2. Yauch, R. L., Felsenfeld, D. P., Kraeft, S-K., Chen, L. B., Sheetz, M. P., & Hemler, M. E. (1997) Mutational evidence for control of cell adhesion through integrin diffusion/clustering, independent of ligand binding. *J. Exp. Med.* 186, 1347-1355.
3. Jakubowski, A., Rosa, M. D., Bixler, S., Lobb, R., & Burkly, L. C. (1995) Vascular cell adhesion molecule (VCAM)-Ig fusion protein defines distinct affinity states of the Very Late Antigen-4 (VLA-4) receptor. *Cell Adhes. Commun.* 3, 131-142.
4. Zhang, Z., Vuori, K., Wang, H-G., Reed, J. C., & Ruoslahti, E. (1996) Integrin activation by R-ras. *Cell* 85, 61-69.
5. D'Souza-Schorey, C., Boettner, B., & van Aelst, L. (1998) Rac regulates integrin-mediated spreading and increased adhesion of T lymphocytes. *Mol. Cell. Biol.* 18, 3936-3946.
6. Van Kooyk, Y., & Figdor, C. G. (2000) Avidity regulation of integrins: the driving force in leukocyte adhesion. *Curr. Opin. Cell Biol.* 12, 542-547.
7. Krissansen, G. W. Integrins: Signalling and disease. The Encyclopedia of Life Sciences. MacMillan Press, 2000.
8. Hughes, P. E., & Pfaff, M. (1998) Integrin affinity modulation. *Trends Cell Biol.* 8, 359-364.
9. Zhang, V. W., Yang, Y., Berg, R. W., Leung, E., Hall, A., & Krissansen, G. W. (1999) The small GTP binding proteins Rho and Rac induce lymphocyte adhesion to the mucosal addressin MAdCAM-1 in an hierarchical fashion. *Eur. J. Immunol.* 29, 2875-2885.
10. Wagner, N., Lohler, J., Kunkel, E. J., Ley, K., Leung, E., Krissansen, G., & Mueller, W. (1996) Critical role for β7 integrins in the formation of the gut associated lymphoid tissue. *Nature* 382, 366-370.
11. Hamann, A., Andrew, D. P., Jablonski-Westrich, B., Holzmann, B., & Butcher, E. C. (1994) The role of a4 integrins in lymphocyte homing to mucosal tissues in vivo. *J. Immunol.* 152, 3282-3293.
12. Yang, X., Sytwn, H-K., McDevitt, H. O., & Michie, S. A. (1997) Involvement of β7 integrin and mucosal addressin cell adhesion molecule-1 (MAdCAM-1) in the development of diabetes in nonobese diabetic mice. *Diabetes* 46, 1542-1547.
13. Kanwar, J. R., Harrison, J. E. B., Wang, D., Leung, E., Wagner, N., Mueller, W., & Krissansen, G. W. (2000) Contributory role for β7 integrins in non-remitting experimental autoimmune encephalomyelitis. *J. Neuroimmunol.* 103, 146-152.
14. Yang, Y., Harrison, J. E. B., Print, C. G., Lehnert, K., Sammar, M., Lazarovits, A., & Krissansen, G. W. (1996) Interaction of monocytoid cells with the mucosal addressin MAdCAM-1 via the integrins VLA-4 and LPAM-1. *Immunol. Cell Biol.* 74, 383-393.
15. Berlin, C., Berg, E. L., Briskin, M. J., Andrew, D. P., Kilshaw, P. J., Holzmann, B., Weissman, I. L., Hamann, A., & Butcher, E. C. (1993) α4β7 integrin mediates lymphocyte binding to the mucosal vascular addressin MAdCAM-1. *Cell* 74, 185-195.

16. Kanwar, J. R., Wang, D., and Krissansen, G. W. (2000) Prevention of a chronic progressive form of experimental autoimmune encephalomyelitis by an antibody against MAdCAM-1, given early in the course of disease progression. *Immunol. Cell Biol.* 78, 641-646.

17. Cepek, K. L., Shaw, S. K., Parker, C. M., Russell, G. J., Morrow, J. S., Rimm, D. L., & Brenner, M. B. (1994) Adhesion between epithelial cells and T lymphocytes mediated by E-cadherin and the αEβ7 integrin. *Nature* 372, 190-193.

18. Karecla, P. I., Bowden, S. J., Green, S. J., & Kilshaw, P. J. (1995) Recognition of E-cadherin on epithelial cells by the mucosal T cell integrin αM290β7 (αEβ7). *Eur. J. Immunol.* 25, 852-856.

19. Hibbs, M. L., Jakes, S., Stacker, S. A., Wallace, R. W., & Springer, T. A. (1991) The cytoplasmic domain of the integrin lymphocyte function-associated antigen 1 beta subunit: sites required for binding to intercellular adhesion molecule 1 and the phorbol ester-stimulated phosphorylation site. *J. Exp. Med.* 174, 1227-1238.

20. Dans, M., Gagnoux-Palacios, L., Blaikie, P., Klein, S., Maiotti, A., & Giancotti, F. G. (2001) Tyrosine phosphorylation of the beta 4 integrin cytoplasmic domain mediates Shc signaling to extracellular signal-regulated kinase and antagonizes formation of hemidesmosomes. *J. Biol. Chem.* 276, 1494-1502.

21. Cowan, K. J., Law, D. A., & Phillips, D. R. (2000) Identification of shc as the primary protein binding to the tyrosine-phosphorylated beta 3 subunit of alpha IIbbeta3 during outside-in integrin platelet signaling. *J. Biol. Chem.* 275, 36423-36429.

22. Mulrooney, J., Foley, K., Vineberg, S., Barreuther, M., & Grabel, L. (2000) Phosphorylation of the beta 1 integrin cytoplasmic domain: toward an understanding of function and mechanism. *Exp. Cell Res.* 258, 332-341.

23. Rietzler, M., Bittner, M., Kolanus, W., Schuster, A., & Holzmann, B. (1998) The human WD repeat protein WAIT-1 specifically interacts with the cytoplasmic tails of β7-integrins. *J. Biol. Chem.* 273, 27459-27466.

24. Yang, Y., Sammar, M., Harrison, J. E. B., Lehnert, K., Print, C. G., Leung, E., Prestidge, R., & Krissansen, G. W. (1995) Construction and adhesive properties of a soluble MAdCAM-1-Fc chimera expressed in a baculovirus system: phylogenetic conservation of receptor-ligand interaction. *Scand. J. Immunol.* 42, 235-247.

25. Lehnert, K., Print, C. G., Yang, Y., & Krissansen, G. W. Mucosal addressin cell adhesion molecule-1 (MAdCAM-1) costimulates T cell proliferation exclusively through integrin α4β7 (LPAM-1), whereas VCAM-1 and CS-1 peptide use α4β1 (VLA-4): Evidence for "remote" costimulation and induction of hyperresponsiveness to B7 molecules. (1998) *Eur. J. Immunol.* 28, 3605-3615.

26. Prochiantz, A. (1996) Getting hydrophilic compounds into cells: lessons from homeopeptides. *Curr. Opinion Neurobiol.* 6, 629-634.

27. Derossi, D., Calvet, S., Trembleau, A., Brunissen, A., Chassaing, G., & Prochiantz, A. (1996) Cell internalization of the third helix of the Antennapedia homeodomain is receptor-independent. *J. Biol. Chem.* 271, 18188-18193.

28. Liu, X-Y., Timmons, S., Lin, Y-Z., & Hawiger, J. (1996) Identification of functionally important sequence in the cytoplasmic tail of integrin β3 by using cell-permeable peptide analogs. *Proc. Natl. Acad. USA* 93, 11819-11824.

29. Yang, Y., Cardarelli, P. M., Lehnert, K., Rowland, S., & Krissansen, G. W. (1998) LPAM-1 (integrin α4β7)-ligand binding: Overlapping binding sites recognising VCAM-1, MAdCAM-1, and CS-1 are blocked by fibrinogen, a fibronectin-like polymer, and RGD-like cyclic peptides. *Eur. J. Immunol.* 28, 995-1004.

30. Mitchell, D. J., Kim, D. T., Steinman, L., Fathman, C. G., & Rothbard, J. B. (2000) Polyarginine enters cells more efficiently than other polycationic homopolymers. *J. Pept. Res.* 56, 318-325.

31. Hughes, P. E., Diazgonzalez, F., Leong, L., Wu, C. Y., McDonald, J. A., Shattil, S. J., & Ginsberg, M. H. (1996) Breaking the integrin hinge. A defined structural constraint regulates integrin signaling. *J. Biol. Chem.* 271, 6571-6574.

32. Bleijs, D. A., Van Duijnhoven, G. C. F., Van Vliet, S. J., Thijssen, J. P. H., Figdor, C. G., & Van Kooyk, Y. (2001) A single amino acid in the cytoplasmic domain of the β2 integrin lymphocyte function-associated antigen-1 regulates avidity-dependent inside-out signaling. *J. Biol. Chem.* 276, 10338-10346.

33. Isakov, N., Wange, R. L., Burgess, W. H., Watts, J. D., Aebersold, R., & Samelson, L. E. (1995) ZAP-70 binding specificity to T cell receptor tyrosine-based activation motifs: the tandem SH2 domains of ZAP-70 bind distinct tyrosine-based activation motifs with varying affinity. *J. Exp. Med.* 181, 375-380.

34. Law, D. A., DeGuzman, F. R., Heiser, P., Ministri-Madrid, K., Killeen, N., & Phillips, D. R. (1999) Integrin cytoplasmic tyrosine motif is required for outside-in αIIbβ3 signalling and platelet function. *Nature* 401, 808-811.

35. Law, D. A., Nannizzi-Alaimo, L., & Phillips, D. R. (1996) Outside-in integrin signal transduction. αIIbβ3-(GPI-IbIIIa) tyrosine phosphorylation induced by platelet aggregation. *J. Biol. Chem.* 271, 10811-10815.

36. Jenkins, A. L., Nannizzi-Alaimo, L., Silver, D., Sellers, J. R., Ginsberg, M. H., Law, D. A., & Phillips, D. R. (1998) Tyrosine phosphorylation of the β3 cytoplasmic domain mediates integrin-cytoskeletal interactions. *J. Biol. Chem.* 273, 13878-13885.

37. Wennerberg, K., Armulik, A., Sakai, T., Karlsson, M., Fassler, R., Schaefer, E. M., Mosher, D. F., & Johansson, S. (2000) The cytoplasmic tyrosines of integrin subunit beta 1 are involved in focal adhesion kinase activation. *Mol. Cell Biol.* 20, 5758-5765.

38. Akiyama, S. K., Yamada, S. S., Yamada, K. M., & LaFlamme, S. E. (1994) Transmembrane signal transduction by integrin cytoplasmic domains expressed in single—subunit chimeras. *J. Biol. Chem.* 269, 15961-15964.

39. Lukashev, M. E., Sheppard, D., & Pytela, R. (1994) Disruption of integrin function and induction of tyrosine phosphorylation by the autonomously expressed β1 integrin cytoplasmic domain. *J. Biol. Chem.* 269, 18311-18314.

40. Chen, Y., O'Toole, T. E., Ylanne, J., Rosa, J., & Ginsberg, M. H. (1994) A point mutation in the integrin β3 cytoplasmic domain (S752-P) impairs bidirectional signaling through αIIbβ3 (platelet glycoprotein IIb-IIIa). *Blood* 84, 1857-1865.

41. LaFlamme, S. E., Akiyama, S. K., & Yamada, K. M. (1992) Regulation of fibronectin receptor distribution. *J. Cell Biol.* 117, 437-447.

42. Zent, R., Fenczik, C. A., Calderwood, D. A., Liu, S., Dellos, M., & Ginsberg, M. H. (2000) Class- and splice variant-specific association of CD98 with integrin β cytoplasmic domains. *J. Biol. Chem.* 275, 5059-5064.

43. Liu, S., Calderwood, D. A., & Ginsberg, M. H. (2000) Integrin cytoplasmic domain-binding proteins. *J. Cell Sci.* 113, 3563-3571.

44. Pfaff, M., Liu, S., Erle, D. J., & Ginsberg, M. H. (1998) Integrin β cytoplasmic domains differentially bind to cytoskeletal proteins. *J. Biol. Chem.* 273, 6104-6109.

45. Sharma, C. P., Ezzell, R. M., & Arnaout, M. A. (1995) Direct interaction of filamin (ABP-280) with the beta 2-integrin subunit CD18. *J. Immunol.* 154, 3461-3470.
46. Loo, D. T., Kanner, S. B., & Aruffo, A. (1998) Filamin binds to the cytoplasmic domain of the β1-integrin. Identification of amino acids responsible for this interaction. *J. Biol. Chem.* 273, 23304-23312.
47. Crowe, D. T., Chiu, H., Fong, S., & Weissman, I. L. (1994) Regulation of the avidity of integrin α4β7 by the β7 cytoplasmic domain. *J. Biol. Chem.* 269, 14411-14418.
48. Diamond B A et al. (1981); *The New England Journal of Medicine,* 1344.
49. Winter, G and Milstein, C. (1991); *Nature,* 349, 293.
50. "Monocolonal Antibody Production Techniques and Applications", Marcel Dekker, Inc: New York, 1987.
51. Holliger P, Prospero T, and Winter G, "Diabodies: small bivalent and bispecific antibody fragments" *Proc Natl Acad Sci USA,* 90, 6444-6448, (1993).
52. Tomlinson I and Holliger P, "Methods for generating multivalent and bispecific antibody fragments", *Methods Enzymol,* 326, 461-479, (2000).
53. "Antibodies a Laboratory Manual", Cold Spring Harbor Laboratory Press (1988).
54. Jones P T, Dear P H, Foote J, Neuberger M S, Winter G. 1986. Replacing the complementarity determining regions in a human antibody with those from a mouse. Nature 321:522-25.
55. Wang et al, J. Immunological Methods 241: 171-184, 2000.
56. Maynard, J., and Georgiou, G. 2000. Antibody engineering. Annu Rev Biomed Eng 2: 339-376.
57. M. W. Hunkapiller, R. M. Hewick, W. J. Dreyer, and L. E. Hood. 1983. High-Sequencing with a Gas-Phase Sequenator. Methods Enzymol. 91: 399.
58. Riechmann L, Clark M, Waldmann H, Winter G. 1988. Reshaping human antibodies for therapy. Nature 332:323-27.

SEQUENCE LISTING

```
<160> NUMBER OF SEQ ID NOS: 39

<210> SEQ ID NO 1
<211> LENGTH: 6
<212> TYPE: PRT
<213> ORGANISM: artificial sequence
<220> FEATURE:
<223> OTHER INFORMATION: residues 735-740 of the transmembrane-proximal
      region of the cytoplasmic tail of the human beta 7 subunit

<400> SEQUENCE: 1

Tyr Asp Arg Arg Glu Tyr
1               5

<210> SEQ ID NO 2
<211> LENGTH: 12
<212> TYPE: PRT
<213> ORGANISM: artificial sequence
<220> FEATURE:
<223> OTHER INFORMATION: A synthetic peptide containing residues 735-740
      of the transmembrane-proximal region of the cytoplasmic tail of
      the human beta 7 subunit

<400> SEQUENCE: 2

Arg Leu Ser Val Glu Ile Tyr Asp Arg Arg Glu Tyr
1               5                   10

<210> SEQ ID NO 3
<211> LENGTH: 9
<212> TYPE: PRT
<213> ORGANISM: artificial sequence
<220> FEATURE:
<223> OTHER INFORMATION: peptide membrane translocation motif from Tat

<400> SEQUENCE: 3

Arg Lys Lys Arg Arg Gln Arg Arg Arg
1               5

<210> SEQ ID NO 4
<211> LENGTH: 21
<212> TYPE: PRT
<213> ORGANISM: artificial sequence
<220> FEATURE:
<223> OTHER INFORMATION: peptide membrane translocation motif from
      Buforin II

<400> SEQUENCE: 4
```

-continued

```
Thr Arg Ser Ser Arg Ala Gly Leu Gln Phe Pro Val Gly Arg Val His
1               5                   10                  15

Arg Leu Leu Arg Lys
            20

<210> SEQ ID NO 5
<211> LENGTH: 26
<212> TYPE: PRT
<213> ORGANISM: artificial sequence
<220> FEATURE:
<223> OTHER INFORMATION: peptide membrane translocation motif from
      transprotan

<400> SEQUENCE: 5

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 6
<211> LENGTH: 18
<212> TYPE: PRT
<213> ORGANISM: artificial sequence
<220> FEATURE:
<223> OTHER INFORMATION: peptide membrane translocation motif from model
      amphipathic peptide (MAP)

<400> SEQUENCE: 6

Lys Leu Ala Leu Lys Leu Ala Leu Lys Ala Leu Lys Ala Ala Leu Lys
1               5                   10                  15

Leu Ala

<210> SEQ ID NO 7
<211> LENGTH: 16
<212> TYPE: PRT
<213> ORGANISM: artificial sequence
<220> FEATURE:
<223> OTHER INFORMATION: peptide membrane translocation motif from K-FGF

<400> SEQUENCE: 7

Ala Ala Val Ala Leu Leu Pro Ala Val Leu Leu Ala Leu Leu Ala Pro
1               5                   10                  15

<210> SEQ ID NO 8
<211> LENGTH: 5
<212> TYPE: PRT
<213> ORGANISM: artificial sequence
<220> FEATURE:
<223> OTHER INFORMATION: peptide membrane translocation motif from Ku70

<400> SEQUENCE: 8

Val Pro Met Leu Lys
1               5

<210> SEQ ID NO 9
<211> LENGTH: 5
<212> TYPE: PRT
<213> ORGANISM: artificial sequence
<220> FEATURE:
<223> OTHER INFORMATION: peptide membrane translocation motif from Ku70

<400> SEQUENCE: 9

Pro Met Leu Lys Glu
1               5
```

```
<210> SEQ ID NO 10
<211> LENGTH: 28
<212> TYPE: PRT
<213> ORGANISM: artificial sequence
<220> FEATURE:
<223> OTHER INFORMATION: peptide membrane translocation motif from Prion

<400> SEQUENCE: 10

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

<210> SEQ ID NO 11
<211> LENGTH: 18
<212> TYPE: PRT
<213> ORGANISM: artificial sequence
<220> FEATURE:
<223> OTHER INFORMATION: peptide membrane translocation motif from pVEC

<400> SEQUENCE: 11

Leu Leu Ile Ile Leu Arg Arg Arg Ile Arg Lys Gln Ala His Ala His
1               5                   10                  15

Ser Lys

<210> SEQ ID NO 12
<211> LENGTH: 21
<212> TYPE: PRT
<213> ORGANISM: artificial sequence
<220> FEATURE:
<223> OTHER INFORMATION: peptide membrane translocation motif from Pep-1

<400> SEQUENCE: 12

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 13
<211> LENGTH: 18
<212> TYPE: PRT
<213> ORGANISM: artificial sequence
<220> FEATURE:
<223> OTHER INFORMATION: peptide membrane translocation motif from SynB1

<400> SEQUENCE: 13

Arg Gly Gly Arg Leu Ser Tyr Ser Arg Arg Arg Phe Ser Thr Ser Thr
1               5                   10                  15

Gly Arg

<210> SEQ ID NO 14
<211> LENGTH: 15
<212> TYPE: PRT
<213> ORGANISM: artificial sequence
<220> FEATURE:
<223> OTHER INFORMATION: peptide membrane translocation motif from Pep-7

<400> SEQUENCE: 14

Ser Asp Leu Trp Glu Met Met Met Val Ser Leu Ala Cys Gln Tyr
1               5                   10                  15

<210> SEQ ID NO 15
<211> LENGTH: 12
<212> TYPE: PRT
<213> ORGANISM: artificial sequence
<220> FEATURE:
```

```
<223> OTHER INFORMATION: peptide membrane translocation motif from HN-1

<400> SEQUENCE: 15

Thr Ser Pro Leu Asn Ile His Asn Gly Gln Lys Leu
1               5                   10

<210> SEQ ID NO 16
<211> LENGTH: 36
<212> TYPE: DNA
<213> ORGANISM: artificial sequence
<220> FEATURE:
<223> OTHER INFORMATION: Nucleotide sequence coding for a synthetic
      peptide containing residues 735-740 of the transmembrane-proximal
      region of the cytoplasmic tail of the  beta 7 subunit

<400> SEQUENCE: 16
cggctctcgg tggaaatcta tgaccgccgg gaatac                                36

<210> SEQ ID NO 17
<211> LENGTH: 18
<212> TYPE: DNA
<213> ORGANISM: artificial sequence
<220> FEATURE:
<223> OTHER INFORMATION: nucleotide sequence for coding residues 735-740
      of the transmembrane-proximal region of the cytoplasmic tail of
      the beta 7 subunit

<400> SEQUENCE: 17
tatgaccgcc gggaatac                                                    18

<210> SEQ ID NO 18
<211> LENGTH: 22
<212> TYPE: PRT
<213> ORGANISM: artificial sequence
<220> FEATURE:
<223> OTHER INFORMATION: peptide membrane translocation motif from beta
      from penetratin

<400> SEQUENCE: 18

Arg Gln Ile Lys Ile Trp Phe Gln Asn Arg Arg Met Lys Trp Lys Lys
1               5                   10                  15

Phe Asp Arg Arg Glu Phe
            20

<210> SEQ ID NO 19
<211> LENGTH: 9
<212> TYPE: PRT
<213> ORGANISM: artificial sequence
<220> FEATURE:
<223> OTHER INFORMATION: a nine-arginine polymer

<400> SEQUENCE: 19

Arg Arg Arg Arg Arg Arg Arg Arg Arg
1               5

<210> SEQ ID NO 20
<211> LENGTH: 6
<212> TYPE: PRT
<213> ORGANISM: Rattus rattus

<400> SEQUENCE: 20

Tyr Asp Arg Leu Glu Tyr
1               5

<210> SEQ ID NO 21
<211> LENGTH: 9
<212> TYPE: PRT
```

```
<213> ORGANISM: artificial sequence
<220> FEATURE:
<223> OTHER INFORMATION: peptide from beta 7

<400> SEQUENCE: 21

Tyr Ser Arg Phe Glu Lys Glu Gln Gln
1               5

<210> SEQ ID NO 22
<211> LENGTH: 19
<212> TYPE: PRT
<213> ORGANISM: artificial sequence
<220> FEATURE:
<223> OTHER INFORMATION: peptide from beta 7

<400> SEQUENCE: 22

Gln Leu Asn Trp Lys Gln Asp Ser Asn Pro Leu Tyr Lys Ser Ala Ile
1               5                   10                  15

Thr Thr Thr

<210> SEQ ID NO 23
<211> LENGTH: 16
<212> TYPE: PRT
<213> ORGANISM: artificial sequence
<220> FEATURE:
<223> OTHER INFORMATION: peptide from beta 7

<400> SEQUENCE: 23

Thr Thr Thr Ile Asn Pro Arg Phe Gln Glu Ala Asp Ser Pro Thr Leu
1               5                   10                  15

<210> SEQ ID NO 24
<211> LENGTH: 7
<212> TYPE: PRT
<213> ORGANISM: artificial sequence
<220> FEATURE:
<223> OTHER INFORMATION: peptide from beta 7

<400> SEQUENCE: 24

Arg Leu Ser Val Glu Ile Tyr
1               5

<210> SEQ ID NO 25
<211> LENGTH: 6
<212> TYPE: PRT
<213> ORGANISM: artificial sequence
<220> FEATURE:
<223> OTHER INFORMATION: peptide from Mutated human beta-7 CARD

<400> SEQUENCE: 25

Phe Asp Arg Arg Glu Phe
1               5

<210> SEQ ID NO 26
<211> LENGTH: 5
<212> TYPE: PRT
<213> ORGANISM: artificial sequence
<220> FEATURE:
<223> OTHER INFORMATION: peptide from beta 7

<400> SEQUENCE: 26

Asp Arg Arg Glu Tyr
1               5

<210> SEQ ID NO 27
<211> LENGTH: 5
<212> TYPE: PRT
```

-continued

```
<213> ORGANISM: artificial sequence
<220> FEATURE:
<223> OTHER INFORMATION: peptide from beta 7

<400> SEQUENCE: 27

Tyr Asp Arg Arg Glu
1               5

<210> SEQ ID NO 28
<211> LENGTH: 17
<212> TYPE: PRT
<213> ORGANISM: artificial sequence
<220> FEATURE:
<223> OTHER INFORMATION: peptide from beta 3-CARD

<400> SEQUENCE: 28

Tyr Lys Glu Ala Thr Ser Thr Phe Thr Asn Ile Thr Tyr Tyr Arg Gly
1               5                   10                  15

Thr

<210> SEQ ID NO 29
<211> LENGTH: 61
<212> TYPE: PRT
<213> ORGANISM: Mus musculus

<400> SEQUENCE: 29

Arg Leu Ser Val Glu Ile Tyr Asp Arg Arg Glu Tyr Arg Phe Glu
1               5                   10                  15

Lys Glu Gln Gln Gln Leu Asn Trp Lys Gln Asp Asn Asn Pro Leu Tyr
            20                  25                  30

Lys Ser Ala Ile Thr Thr Thr Val Asn Pro Arg Phe Gln Gly Thr Asn
        35                  40                  45

Gly Arg Ser Pro Ser Leu Ser Leu Thr Arg Glu Ala Asp
    50                  55                  60

<210> SEQ ID NO 30
<211> LENGTH: 52
<212> TYPE: PRT
<213> ORGANISM: Homo sapiens

<400> SEQUENCE: 30

Arg Leu Ser Val Glu Ile Tyr Asp Arg Arg Glu Tyr Ser Arg Phe Glu
1               5                   10                  15

Lys Glu Gln Gln Gln Leu Asn Trp Lys Gln Asp Ser Asn Pro Leu Tyr
            20                  25                  30

Lys Ser Ala Ile Thr Thr Thr Ile Asn Pro Arg Phe Gln Glu Ala Asp
        35                  40                  45

Ser Pro Thr Leu
    50

<210> SEQ ID NO 31
<211> LENGTH: 58
<212> TYPE: PRT
<213> ORGANISM: Homo sapiens

<400> SEQUENCE: 31

Lys Leu Leu Val Ser Phe His Asp Arg Lys Glu Val Ala Lys Phe Glu
1               5                   10                  15

Ala Glu Arg Ser Lys Ala Lys Trp Gln Thr Gly Thr Asn Pro Leu Tyr
            20                  25                  30

Arg Gly Ser Thr Ser Thr Phe Lys Asn Val Thr Tyr Lys His Arg Glu
        35                  40                  45
```

-continued

Lys Gln Lys Val Asp Leu Ser Thr Asp Cys
    50                  55

<210> SEQ ID NO 32
<211> LENGTH: 57
<212> TYPE: PRT
<213> ORGANISM: Homo sapiens

<400> SEQUENCE: 32

Lys Leu Leu Val Thr Ile His Asp Arg Arg Glu Phe Ala Lys Phe Gln
1               5                   10                  15

Ser Glu Arg Ser Arg Ala Arg Tyr Glu Met Ala Ser Asn Pro Leu Tyr
            20                  25                  30

Arg Lys Pro Ile Ser Thr His Thr Val Asp Phe Thr Phe Asn Lys Phe
        35                  40                  45

Asn Lys Ser Tyr Asn Gly Thr Val Asp
    50                  55

<210> SEQ ID NO 33
<211> LENGTH: 47
<212> TYPE: PRT
<213> ORGANISM: Homo sapiens

<400> SEQUENCE: 33

Lys Leu Leu Ile Thr Ile His Asp Arg Lys Glu Phe Ala Lys Phe Glu
1               5                   10                  15

Glu Glu Arg Ala Arg Ala Lys Trp Asp Thr Ala Asn Asn Pro Leu Tyr
            20                  25                  30

Lys Glu Ala Thr Ser Thr Phe Thr Asn Ile Thr Tyr Arg Gly Thr
        35                  40                  45

<210> SEQ ID NO 34
<211> LENGTH: 46
<212> TYPE: PRT
<213> ORGANISM: Homo sapiens

<400> SEQUENCE: 34

Lys Ala Leu Ile His Leu Ser Asp Leu Arg Glu Tyr Arg Arg Phe Glu
1               5                   10                  15

Lys Glu Lys Leu Lys Ser Gln Trp Asn Asn Asp Asn Pro Leu Phe Lys
            20                  25                  30

Ser Ala Thr Thr Thr Val Met Asn Pro Lys Phe Ala Glu Ser
        35                  40                  45

<210> SEQ ID NO 35
<211> LENGTH: 47
<212> TYPE: PRT
<213> ORGANISM: Homo sapiens

<400> SEQUENCE: 35

Lys Leu Leu Met Ile Ile His Asp Arg Arg Glu Phe Ala Lys Phe Glu
1               5                   10                  15

Lys Glu Lys Met Asn Ala Lys Trp Asp Thr Gly Glu Asn Pro Ile Tyr
            20                  25                  30

Lys Ser Ala Val Thr Thr Val Val Asn Pro Lys Tyr Glu Gly Lys
        35                  40                  45

<210> SEQ ID NO 36
<211> LENGTH: 9
<212> TYPE: PRT
<213> ORGANISM: artificial sequence -continued

```
<220> FEATURE:
<223> OTHER INFORMATION: WAIT-1 binding site  in  beta 7cyt

<400> SEQUENCE: 36

Arg Leu Ser Val Glu Ile Tyr Asp Arg
1               5

<210> SEQ ID NO 37
<211> LENGTH: 4
<212> TYPE: PRT
<213> ORGANISM: artificial sequence
<220> FEATURE:
<223> OTHER INFORMATION: a core sequence in a peptide membrane
      translocation motif from beta 7

<400> SEQUENCE: 37

Asp Arg Arg Glu
1

<210> SEQ ID NO 38
<211> LENGTH: 4
<212> TYPE: PRT
<213> ORGANISM: artificial sequence
<220> FEATURE:
<223> OTHER INFORMATION: a core sequence in a peptide membrane
      translocation motif from beta 2

<400> SEQUENCE: 38

Asp Leu Arg Glu
1

<210> SEQ ID NO 39
<211> LENGTH: 5
<212> TYPE: PRT
<213> ORGANISM: artificial sequence
<220> FEATURE:
<223> OTHER INFORMATION: a motif common to all integrin alpha subunits
      that binds to the beta 2 subunit

<400> SEQUENCE: 39

Gly Phe Phe Lys Arg
1               5
```

The invention claimed is:

1. An isolated peptide consisting of a first segment that includes a core motif having the amino acid sequence YDRREY (SEQ ID NO:1), or a derivative of the first segment, and optionally, a second segment fused to the first segment such that the isolated peptide is a fusion peptide, wherein the second segment is a cell membrane translocating motif that is peptide-based and is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues.

2. An isolated peptide as claimed in claim 1, wherein the cell membrane translocating motif is penetratin or a polymer of arginine.

3. A pharmaceutical composition comprising an isolated peptide consisting of a first segment that includes a core motif having the amino acid sequence YDRREY (SEQ ID NO:1), or a derivative of the first segment, and optionally, a second segment fused to the first segment such that the isolated peptide is a fusion peptide, wherein the second segment is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, together with one or more pharmaceutically acceptable diluents, carriers and/or excipients.

4. A method of modulating the function of integrin β7 in a subject comprising the step of administering to said subject an effective amount of an isolated peptide consisting of a first segment that includes a core motif having the amino acid sequence YDRREY (SEQ ID NO:1), or a derivative of the first segment, and optionally, a second segment fused to the first segment such that the isolated peptide is a fusion peptide, wherein the second segment is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, or a composition comprising the peptide together with one or more pharmaceutically acceptable diluents, carriers or excipients.

5. A method of modulating the function of integrin β7 in an in vitro system comprising the step of administering to said system an isolated peptide consisting of
  a first segment that includes a core motif having the amino acid sequence YDRREY (SEQ ID NO:1) or a derivative of the first segment, and optionally,
  a second segment fused to the first segment such that the isolated peptide is a fusion peptide,
wherein the second segment is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, or a composition comprising the peptide together with one or more pharmaceutically acceptable diluents, carriers or excipients.

6. A method for the treatment of an integrin β7-mediated inflammatory disorder comprising the step of administering to a subject in need thereof a therapeutically effective amount of an isolated peptide consisting of
  a first segment that includes a core motif having the amino acid sequence YDRREY (SEQ ID NO:1), or a derivative of the first segment, and optionally,
  a second segment fused to the first segment such that the isolated peptide is a fusion peptide,
wherein the second segment is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, or a composition comprising the peptide together with one or more pharmaceutically acceptable diluents, carriers or excipients.

7. An isolated peptide consisting of
  a first segment that includes a core motif having the amino acid sequence YDRREY (SEQ ID NO:1), or a derivative of the first segment, and optionally,
  a second segment fused to the first segment such that the isolated peptide is a fusion peptide,
wherein the second segment is heterologous to a β7 integrin cytoplasmic domain, the first segment is conjugated with a cell membrane translocating motif and has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues.

8. An isolated peptide consisting of
  a first segment that includes a core motif having the amino acid sequence YDRREY (SEQ ID NO:1), or a derivative of the first segment, and optionally,
  a second segment fused to the first segment such that the isolated peptide is a fusion peptide,
wherein the second segment is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, and the peptide contains one or more chemically modified or non-naturally occurring amino acid residues.

9. An isolated peptide consisting of
  a first segment that includes a core motif having the amino acid sequence YDRREY (SEQ ID NO:1), or a derivative of the first segment, and optionally,
  a second segment fused to the first segment such that the isolated peptide is a fusion peptide,
wherein the second segment is heterologous to a β7 integrin cytoplasmic domain, the first segment has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, and the peptide is in salt form.

10. A pharmaceutical composition comprising
  a) an isolated peptide consisting of a first segment and optionally, a second segment; and
  b) one or more pharmaceutically acceptable diluents, carriers, or excipients,
wherein the first segment has a maximum length of 13 amino acid residues and is a fragment of integrin β7 that includes the core motif YDRREY (SEQ ID NO:1) and 1-6 additional amino acid residues at either the N- or the C-terminus of the core motif, and the second segment is heterologous to the core motif.

11. A pharmaceutical composition as claimed in claim 10, wherein the first segment consists of the amino acid sequence RLSVEIYDRREY (SEQ ID NO:2).

12. A pharmaceutical composition as claimed in claim 10, wherein the peptide includes both the first segment and the second segment.

13. A pharmaceutical composition as claimed in claim 10, wherein the peptide consists of the first segment that is conjugated with a cell membrane translocating motif.

14. A method for modulating the function of integrin β7 in a subject comprising the step of administering to said subject an effective amount of a) a peptide consisting of a first segment and optionally a second segment, or b) a composition that includes the peptide together with one or more pharmaceutically acceptable diluents, carriers, or excipients,
wherein the first segment has a maximum length of 13 amino acid residues and is a fragment of integrin β7 that includes the core motif YDRREY (SEQ ID NO:1) and 1-6 additional amino acid residues at either the N- or the C-terminus of the core motif, and the second segment is heterologous to the core motif.

15. A method for modulating the function of integrin β7 as claimed in claim 14, wherein the first segment consists of the amino acid sequence RLSVEIYDRREY (SEQ ID NO:2).

16. A method for modulating the function of integrin β7 as claimed in claim 4, wherein the peptide includes both the first segment and the second segment.

17. A method for modulating the function of integrin β7 as claimed in claim 4, wherein the peptide consists of the first segment that is conjugated with a cell membrane translocating motif.

18. A method for modulating the function of integrin β7 in an in vitro system comprising the step of administering to said system a) a peptide consisting of a first segment and optionally a second segment, or b) a composition that includes the peptide together with one or more pharmaceutically acceptable diluents, carriers, or excipients,
wherein the first segment has a maximum length of 13 amino acid residues and is a fragment of integrin β7 that includes the core motif YDRREY (SEQ ID NO:1) and 1-6 additional amino acid residues at either the N- or the C-terminus of the core motif, and the second segment is heterologous to the core motif.

19. A method for modulating the function of integrin β7 as claimed in claim 18, wherein the first segment consists of the amino acid sequence RLSVEIYDRREY (SEQ ID NO:2).

20. A method for modulating the function of integrin β7 as claimed in claim 5, wherein the peptide includes both the first segment and the second segment.

21. A method for modulating the function of integrin β7 in an in vitro system comprising the step of administering to said system a) a peptide, or b) a composition that includes the peptide together with one or more pharmaceutically acceptable diluents, carriers, or excipients,
wherein the peptide consists of a segment that is conjugated with a cell membrane translocating motif, the segment includes a core motif having the amino acid sequence YDRREY (SEQ ID NO:1), and the segment has a maximum length of 13 amino acid residues.

22. A method for the treatment of an integrin β7-mediated inflammatory disorder comprising the step of administering to a subject in need thereof a therapeutically effective amount of a) a peptide consisting of a first segment and optionally a second segment, or b) a composition that includes the peptide together with one or more pharmaceutically acceptable diluents, carriers, or excipients,
wherein the first segment has a maximum length of 13 amino acid residues and is a fragment of integrin β7 that includes the core motif YDRREY (SEQ ID NO:1) and 1-6 additional amino acid residues at either the N- or the C-terminus of the core motif, and the second segment is heterologous to the core motif.

23. A method for the treatment of an integrin β7-mediated inflammatory disorder as claimed in claim 22, wherein the first segment consists of the amino acid sequence RLSVEIYDRREY (SEQ ID NO:2).

24. A method for the treatment of an integrin β7-mediated inflammatory disorder as claimed in claim 6, wherein the peptide includes both the first segment and the second segment.

25. A method for the treatment of an integrin β7-mediated inflammatory disorder as claimed in claim 6, wherein the peptide consists of the first segment that is conjugated with a cell membrane translocating motif.

26. A kit for modulating the function of integrin β7 or for the treatment of integrin β7-mediated inflammatory disorders, the kit comprising at least an isolated peptide consisting of
a first segment that includes a core motif having the amino acid sequence YDRREY (SEQ ID NO:1), or a derivative of the first segment, and optionally,
a second segment fused to the first segment such that the isolated peptide is a fusion peptide,
wherein the second segment is heterologous to a β7 integrin cytoplasmic domain, the first segment is conjugated with a cell membrane translocating motif and has a maximum length of 13 amino acid residues, and the derivative has a maximum length of 13 amino acids and includes an amino acid sequence containing two Y residues which differs from the amino acid sequence YDRREY (SEQ ID NO:1) by one and only one of (a) a conservative amino acid substitution for at least one of the D, R, R, and E residues, and (b) one, two, or three deletions of the D, R, R, and E residues, or a composition comprising the peptide together with one or more pharmaceutically acceptable diluents, carriers or excipients.

27. The isolated peptide of claim 1, wherein the first segment consists of the amino acid sequence RLSVEIYDRREY (SEQ ID NO:2).

* * * * *